United States Patent
Zou et al.

(10) Patent No.: US 7,088,457 B1
(45) Date of Patent: Aug. 8, 2006

(54) ITERATIVE LEAST-SQUARES WAVEFRONT ESTIMATION FOR GENERAL PUPIL SHAPES

(75) Inventors: Weiyao Zou, Orlando, FL (US); Jannick P. Rolland, Chuluota, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 254 days.

(21) Appl. No.: 10/867,527

(22) Filed: Jun. 10, 2004

Related U.S. Application Data

(60) Provisional application No. 60/507,657, filed on Oct. 1, 2003.

(51) Int. Cl.
G01B 9/02 (2006.01)
G01B 9/00 (2006.01)

(52) U.S. Cl. ...................... 356/512; 356/124
(58) Field of Classification Search ............ 356/511, 356/512, 124–127
See application file for complete search history.

(56) References Cited

U.S. PATENT DOCUMENTS

| | | | | |
|---|---|---|---|---|
| 4,804,269 A * | 2/1989 | Elterman | ............ | 356/520 |
| 5,864,381 A * | 1/1999 | Neal et al. | ............ | 351/205 |
| 6,184,974 B1 * | 2/2001 | Neal et al. | ............ | 356/121 |
| 6,956,657 B1 * | 10/2005 | Golini et al. | ............ | 356/512 |
| 2004/0130705 A1 * | 7/2004 | Topa | ............ | 356/121 |
| 2006/0071155 A1 * | 4/2006 | Chen | ............ | 250/221 |

OTHER PUBLICATIONS

Zou and Zhang, Generalized Wave-Front Reconstruction Algorithm Applied in a Shack-Hartmann Test, Jan. 10, 2000, p. 250-268, *Applied Optics*/vol. 39, No. 2.

* cited by examiner

*Primary Examiner*—Hoa Q. Pham
*Assistant Examiner*—Patrick Connolly
(74) *Attorney, Agent, or Firm*—Brian S. Steinberger; Law Offices of Brian S. Steinberger, P.A.

(57) ABSTRACT

Iterative algorithm methods and systems for slope or gradient-type data is presented for wavefront zonal estimation of regular and irregular pupil shapes. The methods and systems bears universal wavefront estimation matrices that are directly applicable to any pupil shape without the need to set up new matrices. The algorithm consists in first extending the sampling pupil to a larger regular square shape and second extrapolating the sampled slope data outside of the sampling pupil employing Gerchberg-type iterations. Unbiased least-squares wavefront estimation is then performed in the square domain. Results show that the RMS deviation error of the estimated wavefront from the original wavefront can be less than $\lambda/150$ after about twelve iterations and less than $\lambda/100$ (both for $\lambda$ equal 632.8 nm) within as few as five iterations.

14 Claims, 24 Drawing Sheets i=0, rms= λ/16 i=1, rms=λ/37 i=2, rms=λ/63 i=3, rms=λ/86 i=4, rms=λ/105 i=13, rms=λ/129 i=0, rms=λ/14 i=1, rms=λ/26 i=3, rms=λ/63 i=5, rms=λ/107 i=7, rms=λ/135

ITERATIVE LEAST-SQUARES WAVEFRONT ESTIMATION FOR GENERAL PUPIL SHAPES

This invention claims the benefit of priority to U.S. Provisional Application 60/507,657 filed Oct. 1, 2003, and this invention was funded in part by the National Science Foundation IIS/HCI-0307189.

FIELD OF USE

This invention relates generally to optical aberration analysis and more particularly to methods and systems to reconstruct a wavefront from slope data based on a domain-extended iterative linear least squares technique and method.

BACKGROUND AND PRIOR ART

Wavefront estimation, or equivalently wavefront reconstruction, from measured wavefront slope data is a classic problem in optical testing, active/adaptive optics, and media turbulence characterizations. It converts the wavefront slope data to wavefront optical path differences (OPDs) or wavefront phase estimates by multiplying the OPDs by $2\pi/\lambda$. The OPDs shall be referred to as the wavefront values. The wavefront slope data is obtained from a slope wavefront sensor, and the task is to find a solution to the Neumann boundary problem of Poisson's equation.

Mathematical methods and algorithms for wavefront reconstruction in optical testing have been contributed by many authors. Approaches to wavefront reconstruction from slope data can be categorized as either zonal or modal estimation. In modal estimation, the wavefront is estimated by computing the coefficients of an aperture function with an orthogonal basis, whereas in zonal estimation, the wavefront is estimated by evaluating the wavefront values in local zones. In either case, a wavefront reconstruction is a least-squares estimate to the wavefront values, a numerical solution to the Neumann boundary problem. Only certain algorithms can handle general pupil shapes. These algorithms can be categorized into the Fourier-transform (FT)-based algorithms and the linear least-squares (LS)-based algorithms. By way of example, Gerchberg et al. pioneered the iterative Fast Fourier-Transform (FFT)-based phase retrievals from amplitude measurements in the aperture and the image planes in "A practical algorithm for the determination of phase from image and diffraction plane pictures", as published in *Optik*, Volume 35, pages 237–246, 1972. Freischlad et al. disclosed a Discrete Fourier Transform (DFT)-based algorithm for zonal estimation from wavefront slope measurements for square-shaped pupils in "Wavefront Reconstruction From Noisy Slope or Difference Data Using the Discrete Fourier Transform", published in Adaptive Optics, J. E. Ludman, ed., Proceedings of the SPIE, Volume 551, pages 74–80, 1985; and in "Modal Estimation of a Wavefront Difference Measurements Using the Discrete Fourier Transform", published in the Journal of the Optical Society of America A, Volume 3, No. 11, pages 1852–1861, 1986.

Later, Freischlad extended this algorithm for general pupil shapes as described in "Wavefront Integration From Difference Data", as published in Interferometry: Techniques and Analysis, G. M. Brown, O. Y. Kwon, M. Kujawinska, and G. T. Reid, Eds., Proceedings of the SPIE, Volume 1755, pages 212–218, 1992. In Freischlad's method, additional Least-Squares matrix equations needed to be set up to generate the missing slope data for extending the general shaped pupil to a square one. Roddier et al. disclosed a technique to extrapolate the wavefront outside of the pupil employing Gerchberg-type iterations and obtained an excellent FFT-based algorithm for irregular shaped pupils in "Interferogram Analysis Using Fourier Transform Techniques", as published in Applied Optics, Volume 26, No. 9, pages 1668–1673, 1987; and in "Wavefront Reconstruction Using Iterative Fourier Transforms" as published in Applied Optics, Volume 30, No. 11, pages 1325–1327, 1991.

Recently an application of FFT-based algorithms for large adaptive optics systems was disclosed by Lisa Poyner et al. in "Fast Wavefront Reconstruction in Large Adaptive Optics Systems with use of the Fourier Transform", as published in Journal of the Optical Society of America A, Volume 19, No. 10, pages 2100–2111, 2002.

For linear LS-based algorithms, Zou et al. proposed an efficient generalized algorithm with zero-padding of the slope data outside of the sampling pupil in "Generalized Wavefront Reconstruction Algorithm Applied in a Shack-Hartmann Test", as published in Applied Optics, Volume 39, No. 2, pages 250–268, 2000. This algorithm is efficient given that it uses a regular and symmetrical reconstruction matrix as well as the efficient Cholesky Decomposition method in solving the large sparse linear equation set. However, the wavefront reconstructed with this algorithm leads to up to $\lambda/4$ deviation errors (peak-to-valley) with a corresponding rms error of about $\lambda/14$ from the original. While the deviation errors vary with the smoothness of the wavefront under construction. The $\lambda/4$ deviation errors may not be acceptable for many optical tests.

Recently Ellerbroek disclosed a minimum-variance wavefront reconstructor for adaptive optics utilizing sparse matrix techniques in "Efficient Computation of Minimum-Variance Wavefront Reconstructors with Sparse Matrix Techniques", as published in the Journal of the Optical Society of America A, Volume 19, No. 9, pages 1803–1816, 2002. A multigrid preconditioned conjugate-gradient method was proposed by Gilles et al. for the reconstructor computation in "Multi-grid preconditioned conjugated-gradient method for large-scale wavefront reconstruction" as published in the Journal of the Optical Society of America A, Volume 19, No. 9, pages 1817–1822, 2002.

These methods are efficient for large adaptive optics (AO) systems and multi-conjugated adaptive optics (MCAO) systems and may also find application to wavefront estimation given that such step is implicit to the wavefront reconstructor. Also, MacMartin recently disclosed a local, hierarchic and iterative reconstructor for adaptive optics in "Local, Hierachic, and Iterative Reconstructors for Adaptive Optics," as published in the Journal of the Optical Society of America, Volume 20, No 6, pages 1084–1093 (2003), which is related to the multigrid preconditioning method used in Gilles et al. MacMartin's algorithm, which is based on modal estimation, shows excellent (i.e. results approach relatively closely an optimal least-squares solution) relative performance across the Zernike basis function used to estimate the wavefront.

A main difference between wavefront estimation for AO and optical testing is that estimation errors above the bandwidth of the control loop can not be corrected in AO, and the common geometry used in AO is the Fried geometry. Nevertherless, several of the computationally efficient algorithms for wavefront reconstruction developed in the context of AO may find application to the optical testing problem with, in the case where modal estimation was used, an adjustment of the basis functions to satisfy orthogonality conditions across the pupil shape.

However, most of the algorithms in the prior art require setting up of the reconstruction procedure (e.g. setting up of matrices) before they can accept wavefront sensor (WFS) measurements. A process that could be fully automated is desirable in optical testing because of the frequent change in pupil sizes and shapes.

Also, the number of sampling grid points will vary significantly from a grid as small as a 4×4 points to thousands of points depending on the local curvature of the piece under test and its physical size. The trade-off is that a non-automatic procedure can perhaps better capitalize on the specific problem and optimize the reconstructor for speed for a given pupil shape and size. In cases where speed is not absolutely critical for a given pupil shape and size, but rather accuracy is the dominant performance metric and within a day various pupil shapes and sizes are tested, the establishment of a universal matrix that can accept any dataset from any pupil shape and size would be a tremendous gain. While a strength of the linear LS approach by Zou et al. is a universal normal matrix of wavefront reconstruction that provides immediate plug-in of WFS measurements for any pupil shapes and pupil sizes, the associated algorithm suffers remarkable deviation errors.

The present invention improves on the Zou et al. algorithm by reducing the deviation errors with Gerchberg-type iterations that enable extrapolating the slope data outside of the pupil to satisfy continuity boundary conditions. The approach of employing Gerchberg-type iterations in wavefront reconstruction, as Roddier et al. did with a DFTs-based method, is remarkable when combined with a linear LS method as disclosed in this invention in terms of the accuracy achieved and the convergence rate towards a solution. Moreover, because the linear LS approach yields a universal matrix regardless of the size of the input slope data set, it provides practical convenience in optical testing applications.

SUMMARY OF THE INVENTION

The first objective of the present invention is a method to reconstruct a wavefront from slope-type or gradient-type data.

The second objective of the present invention is a method of wavefront reconstruction that reduces deviation errors introduced by domain extension.

The third objective of the present invention is a method of wavefront reconstruction that provides an efficient convergence rate.

The fourth objective of the present invention is to provide a universal reconstruction matrix for any irregular pupil shape and size.

The fifth objective of the present invention is a method of wavefront reconstruction that provides low error propagation.

The sixth objective of the present invention is to provide unbiased least-squares wavefront estimation.

The present invention introduces an iterative procedure and presents a new generalized wavefront reconstruction algorithm. This iterative procedure bears an analogy to the Gerchberg-Saxton algorithm. The algorithm consists in first extending the sampling pupil to a larger regular square shape and second extrapolating the sampled slope data outside of the sampling pupil employing Gerchberg-type iterations. Unbiased least-squares wavefront estimation is then performed in the square domain. Results show that the RMS deviation error of the estimated wavefront from the original wavefront can be less than $\lambda/150$ after about twelve iterations and less than $\lambda/100$ (both for $\lambda$ equal 632.8 nm) within as few as five iterations.

Further objects and advantages of this invention will be apparent from the following detailed description of the presently preferred embodiments which are illustrated schematically in the accompanying drawings.

DESCRIPTION OF THE PREFERRED EMBODIMENTS

Before explaining the disclosed embodiments of the present invention in detail, it is to be understood that the invention is not limited in its application to the details of the particular arrangements shown since the invention is capable of other embodiments. Also, the terminology used herein is for the purpose of description and not of limitation.

Figure 1A:
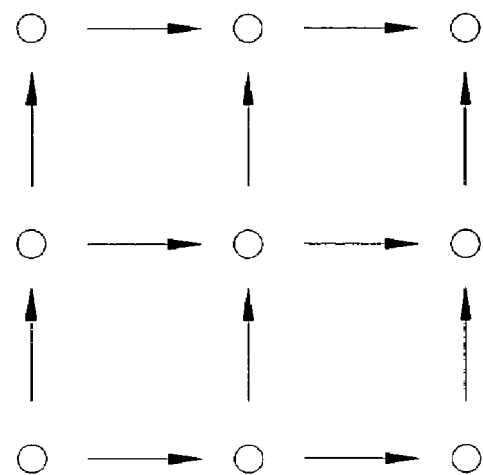
FIG. 1a shows the Hudgin wavefront reconstruction scheme.
Figure 1B:
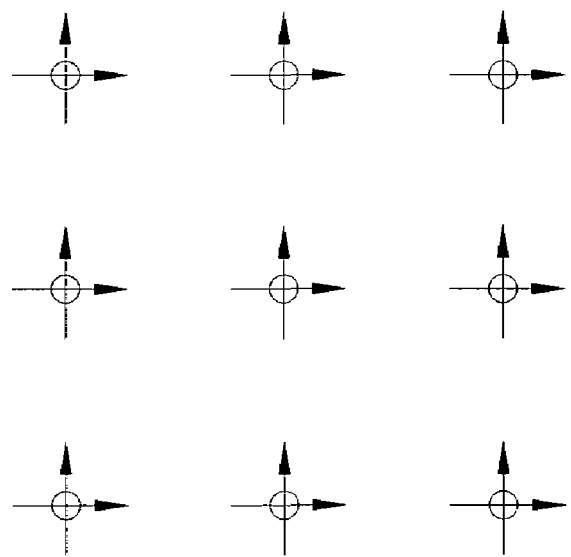
FIG. 1b shows the Southwell wavefront reconstruction scheme.
Figure 1C:
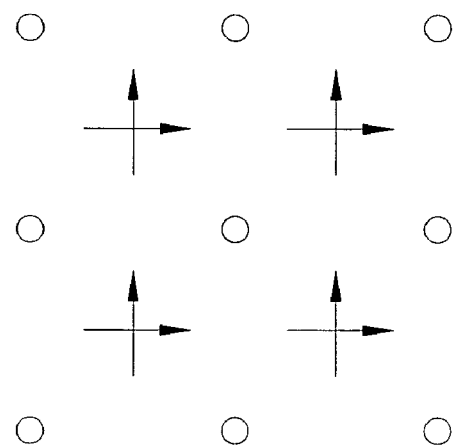
FIG. 1c shows the Fried wavefront reconstruction scheme.

As discussed above, Zou et al. disclosed a non-iterative linear LS method based on a domain extension technique to perform wavefront estimation. The disclosed algorithm was motivated by the need, in practical settings, to automate the reconstruction process regardless of the pupil shapes considered and the input measurement arrays. Regardless of the method adopted, a sampling geometry had to be first considered in performing wavefront estimation. There are basically three sampling geometries available for zonal estimates: the Hudgin geometry, a shown in FIG. 1a; the Southwell geometry, as shown in FIG. 1b; and the Fried geometry, as shown in FIG. 1c.

Due to its superiority over other geometries in error propagation, Zou et al. adopted the Southwell model. However, the present invention is directly applicable to the Hudgin and the Fried Models, it is by no means restricted to the Southwell model. The Southwell geometry is characterized by taking the wavefront slope measurements and wavefront values estimation at the same nodes. In a problem with discrete slope measurements as a starting point, a 2-D y-z array of discrete values $w_i$ (i=1, 2, 3, . . . t×t) was used to map the estimated wavefront values, and an interlaced array of j nodes was introduced to facilitate the estimations of wavefront slopes at the midpoints between wavefront nodes.

Figure 2:
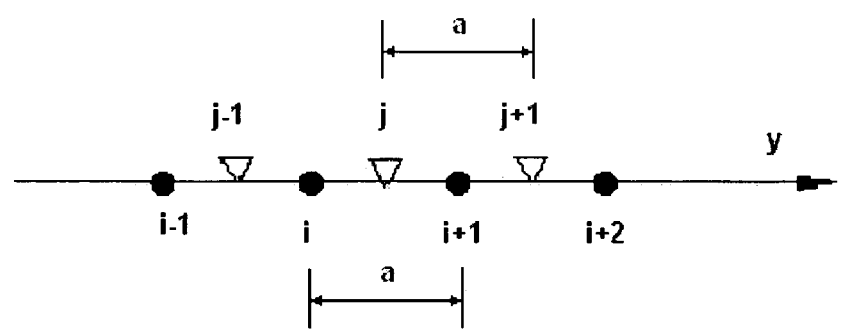
FIG. 2 is a schematic illustration of double sampling grid systems shown in the y-direction.

FIG. 2 shows the geometry in the y-direction with both the wavefront nodes i and the interlaced nodes j. The wavefront slopes at the nodes i in the y and z directions are denoted as $s_{y_i}$ and $s_{z_i}$ (i=1, 2, 3 . . . t×t), respectively. The slope data between two adjacent nodes was assumed to change linearly with distance, which allows linear interpolation to estimate the slopes between nodes. The slope at node j was then estimated as an average of the slopes at nodes i and i+1 by:

$$s_{yj} = \frac{1}{2}(s_{y_i} + s_{y_{i+1}}), \quad (1)$$

where the slope $s_{yj}$ could also be expressed as the difference quotient of the wavefront values at nodes i and i+1 to their separation a, so that $$s_{yj} = \frac{w_{i+1} - w_i}{a}. \quad (2)$$

By combining Equations (1) and (2), a relationship between the wavefront slopes and the wavefront values at i+1 and i was established as $$w_{i+1} - w_i = \frac{a}{2}(s_{y_i} + s_{y_{i+1}}). \quad (3)$$

Similarly in the z direction and accounting for the sign convention shown in FIG. 2, $$w_i - w_{i+t} = \frac{a}{2}(s_{zi} + s_{zi+t}). \quad (4)$$

Figure 3:
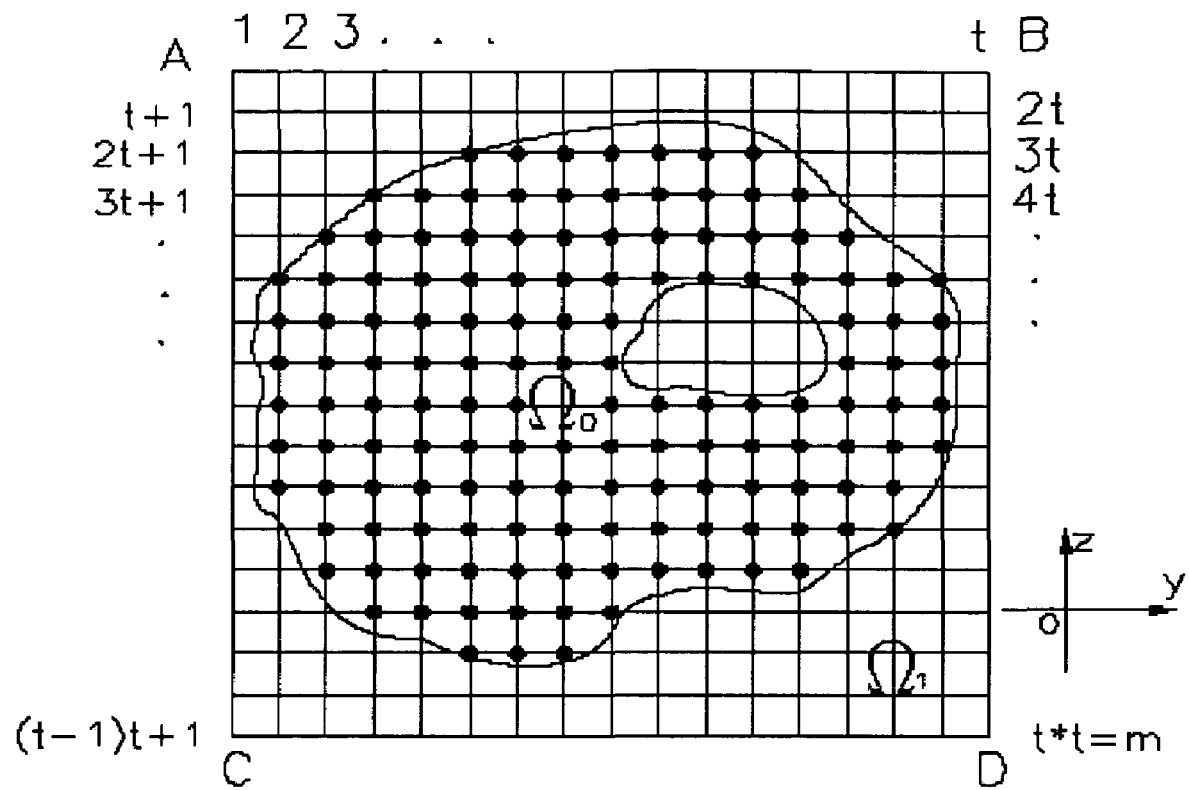
FIG. 3 illustrates the domain extension of an irregular-shaped pupil.

In order to develop a universal (i.e. applicable to any pupil shape) wavefront reconstruction algorithm, the following steps were followed by Zou et al.:

1. Without loss of generality, assume that the regular square net has t×t=m grid points.
2. The original sampling domain $\Omega_0$ (i.e. exit pupil, simply connected domain or multiple connected domains) was embedded into a regular square domain $\Omega_1$ that contains the sampling domain $\Omega_0$. Then the square domain $\Omega_1$ was thought of being composed of two parts: the real part $\Omega_0$ and the imaginary part $\Omega_1 \backslash \Omega_0$, as shown in FIG. 3.
3. The grid points in $\Omega_1$ were indexed sequentially from 1 to m row by row (the grid points could also be indexed equivalently column by column as an alternative).
4. The slopes were set to zero in the imaginary part $\Omega_1 \backslash \Omega_0$.

From the geometry adopted, Equations (3) and (4) may be written in matrix form as:

$$\begin{bmatrix} -1 & 1 & & & & & & & & & \\ & -1 & 1 & & & & & & & & \\ & & \ddots & \ddots & & & & & & & \\ & & & -1 & 1 & & & & & & \\ & & & & -1 & 1 & & & & & \\ & & & & & \ddots & \ddots & & & & \\ & & & & & & -1 & 1 & & & \\ & & & & & & & \ddots & \ddots & & \\ & & & & & & & & -1 & 1 & \\ & & & & & & & & & -1 & 1 \\ & & & & & & & & & \ddots & \ddots \\ & & & & & & & & & & -1 & 1 \\ 1 & 0 & 0 & \cdots & 0 & -1 & & & & & & \\ & 1 & 0 & 0 & \cdots & 0 & -1 & & & & & \\ & & \ddots & \ddots & & & \ddots & \ddots & & & & \\ & & & & & & & & \ddots & \ddots & & \\ & & & & & & & 1 & 0 & 0 & \cdots & 0 & -1 \\ & & & & & & & & 1 & 0 & 0 & \cdots & 0 & -1 \end{bmatrix} \begin{bmatrix} w_1 \\ w_2 \\ \vdots \\ w_t \\ w_{t+1} \\ w_{t+2} \\ \vdots \\ w_{2t} \\ \vdots \\ w_{m-2t+1} \\ w_{m-2t+2} \\ \vdots \\ w_{m-t} \\ w_{m-t+1} \\ \vdots \\ w_{m-1} \\ w_m \end{bmatrix} = \begin{bmatrix} c_{2,1} \\ c_{3,2} \\ \vdots \\ c_{t,t-1} \\ c_{t+2,t+1} \\ \vdots \\ \vdots \\ c_{m-1,m} \\ d_{t+1,t} \\ d_{t+2,t} \\ \vdots \\ d_{2t,t} \\ \vdots \\ d_{i+t,i} \\ \vdots \\ d_{m-1,m-t-1} \\ d_{m,m-t} \end{bmatrix},$$ (5a)

or $$CW=S,$$ (5b)

where $C_{i+1,i}$ and $d_{i+1,i}$ are defined as $$c_{i+1,i} = \frac{a}{2}(s_{y_{i+1}} + s_{y_i}),$$ (6a)

$$d_{i+t,i} = \frac{a}{2}(s_{z_{i+t}} + s_{z_i}).$$ (6b)

The corresponding normal equation set can be written as $$C^T C W = C^T S.$$ (7)

Such an algorithm was applied successfully in achieving efficient wavefront estimation; however results were limited by up to λ/4 peak-to-valley deviation errors.

Wavefront Estimation for any Pupil Shape: a Gerchberg-Type Iterative Linear Least-Squares Approach The present invention expands on the method of Zou et al. and presents an iterative procedure to improve the accuracy of the final wavefront estimation within the measured pupil. The merit of the iterative procedure is that it yields negligible RMS deviation errors while it still provides a universal reconstruction matrix for any irregular pupil shape and size. In such an approach, all the matrix coefficients are determined and known once and for all. Furthermore, the matrix is sparse, symmetrical, and regular and the matrix elements can be expressed as a function of the matrix index using the Kronecker's delta function. The algorithm detailed hereafter will first require calculating slope data from the estimated wavefront in order to enable the iterative process. Such computations will be first presented.

Slope computation from a known wavefront may be thought simply as the inverse problem of wavefront estimation from slope data. The equations established by Zou et al. can be inverted to obtain a matrix equation set for slope extraction. However, the matrix developed out of these reversed equations is rank-deficient for estimating the slope data from the reconstructed wavefront. Such a finding is intrinsically linked to the Southwell geometry chosen for the problem. Thus, additional independent equations are required. Such equations will be based on curvature estimates, and the equations for slope computation will thus be grouped into two types: slope-based and curvature-based. The matrix for extracting the y-direction slopes will first be described. The matrix for extracting the z-direction slopes will then be provided.

For the slope in the y-direction at the midpoint between the nodes i and i+1, Equation (3) may be written as $$s_{y_{i+1}} + s_{y_i} = e_j,$$ (8)

where $$e_j = \frac{2}{a}(w_{i+1} - w_i), \ i = 1, 2 \ldots m-1, \text{ but } i \neq t, 2t, 3t, \ldots m$$ (9)

In matrix form, Equation (8) may be written as $$A_1 S_y = E,$$ (10)

which is not a full-rank matrix equation set. Curvature-based equations are then considered to determine a unique solution for slope extraction. The curvature at a midpoint node j+1 is proportional to the slope difference between adjacent points i+1 and i+2. According to FIG. 1:

$$s_{y_{i+2}} - s_{y_{i+1}} = f_{j+1},$$ (11)

where $$f_{j+1} = \left(\frac{w_{i+3} - w_{i+1}}{2a} - \frac{w_{i+2} - w_i}{2a}\right)$$ (12)

$$= \frac{1}{2a}(w_{i+3} - w_{i+2} - w_{i+1} + w_i).$$

If Equation (12) is divided by the grid separation a, it will actually be a discrete approximation of wavefront curvature at node j+1, which is of $O(a^3)$ precision as shown in Equation (A12). In matrix form, Equation (11) may be expressed as $$A_2 S_y = F. \tag{13}$$

Combining Equations (10) and (13), a unified form may be written as $$A S_y = U, \tag{14}$$

where $$A = \begin{bmatrix} A_1 \\ A_2 \end{bmatrix}, \tag{15}$$

$$S_y = [s_{y1}\, s_{y2} \ldots s_{ym}]^T, \tag{16}$$

$$U = \begin{bmatrix} E \\ F \end{bmatrix}, \tag{17}$$

with $$A_1 = \text{diag}[D_1, D_1, \ldots, D_1]^e, \tag{18}$$

$$A_2 = \text{diag}[D_2, D_2, \ldots, D_2]^e, \tag{19}$$

where $$D_1 = \begin{bmatrix} 1 & 1 & & & \\ & 1 & 1 & & \\ & & \ddots & \ddots & \\ & & & 1 & 1 \end{bmatrix}_{(t-1) \times t}, \tag{20}$$

and $$D_2 = \begin{bmatrix} -1 & 1 & & & \\ & -1 & 1 & & \\ & & \ddots & \ddots & \\ & & & -1 & 1 \\ & & & & -1 & 1 \end{bmatrix}_{(t-3) \times t}. \tag{21}$$

Then the normal equation set for the wavefront slope extraction in the y-direction can be written as $$A^T A S_y = A^T U. \tag{22}$$

Similarly, the slope-based equations along the z-direction are given by $$s_{z,i} + s_{z,i+1} = g_j,\ i=1, 2, \ldots, m-t, \tag{23}$$

$$g_j = \frac{2}{a}(w_i - w_{i+1}). \tag{24}$$

where

In matrix form, Equation (23) may be written as $$B_1 S_z = G \tag{25}$$

which is not a full-rank matrix equation. To get a full-rank equation set, we add the curvature-based equations $$s_{z,i+t} - s_{z,i+2t} = h_{j+t}, \tag{26}$$

where $$h_{j+t} = \frac{1}{2a}(w_i - w_{i+t} - w_{i+2t} + w_{i+3t}), \tag{27}$$

and i=1,2, ... t; t+1, t+2, ... 2t−3, ... , m−3t. The derivation of Equation (27) is shown by Equation (A14).

In matrix form, Equation (26) becomes $$B_2 S_z = H. \tag{28}$$

Combining Eqs. (25) and (28) in a matrix-form equation set, we obtain $$B S_z = V, \tag{29}$$

$$B = \begin{bmatrix} B_1 \\ B_2 \end{bmatrix}, \tag{30}$$

where $$S_z = [s_{z1}\, s_{z2} \ldots s_{zm}]^T \tag{31}$$

$$V = \begin{bmatrix} G \\ H \end{bmatrix}, \tag{32}$$

and $$B_1 = \begin{bmatrix} I_t & I_t & & & \\ & I_t & I_t & & \\ & & \ddots & \ddots & \\ & & & I_t & I_t \\ & & & & I_t & I_t \end{bmatrix}, \tag{33}$$

$$B_2 = \begin{bmatrix} I_t & -I_t & & & \\ & I_t & -I_t & & \\ & & \ddots & \ddots & \\ & & & I_t & -I_t \\ & & & & I_t & -I_t \end{bmatrix}, \tag{34}$$

$$I_t = \begin{bmatrix} 1 & & & \\ & 1 & & \\ & & \ddots & \\ & & & 1 \end{bmatrix}_{t \times t}. \quad (35)$$

Then the normal equation set for the z-direction slope extraction may be written as $$B^T B S_z = B^T V. \quad (36)$$

Gerchberg-Type Iterative Wavefront Estimation Algorithm

Figure 4:
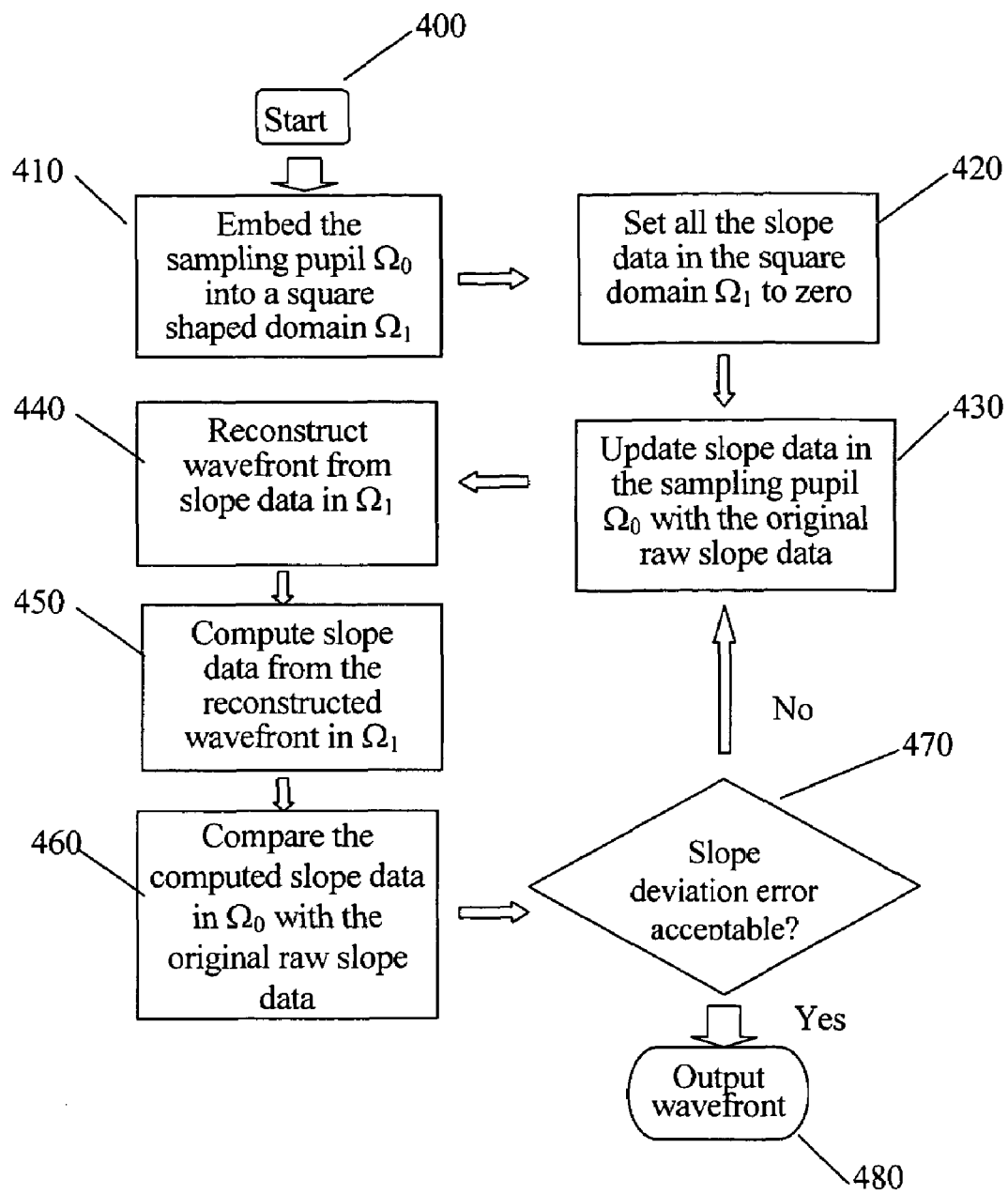
FIG. 4 is a flow chart of the Gerchberg-type iterative least-squares wavefront estimation algorithm based on the domain extension technique.

Based on the equation sets just established for wavefront slope computations, combined with the algorithm of wavefront reconstruction from slope data given by Zou et al., the new iterative LS wavefront reconstruction algorithm, illustrated in the flow diagram of FIG. 4, will now be detailed.

Using Equation (7), the wavefront is reconstructed from slope data in $\Omega_1$ 410. The matrix equation sets given by Equations (22) and (36) are used to compute they and z slopes in $\Omega_1$ from the reconstructed wavefront 440. The computed slopes 450 are compared with the original slope data within $\Omega_0$ 460. If the differences are negligible (i.e. less than a termination criterion) 470, the reconstructed wavefront over $\Omega_1$ is output 480, among which only the wavefront within $\Omega_0$ is of interest. Otherwise, the slope data in $\Omega_0$ are replaced with the original measured slope data 430, while the slope data in the extended area $\Omega_1 \backslash \Omega_0$ are kept unchanged. The iterative process continues until it satisfies the established termination criterion.

Such iterative processes are referred to as the Gerchberg-type iterations, because the iterative process bears analogy to the Gerchberg-Saxton algorithm, which consists in substituting the computed amplitude of a discrete complex function in the pupil under test with the sampled amplitude across iterations, until both amplitude and phase converged to a solution. The iterative algorithm presented in this invention substitutes the slope data in the pupil under test with the sampled raw slope data iteratively until the reconstructed wavefront converges to a unique solution. In a fundamental sense, the Gerchberg-Saxton iterations were based on Fourier transforms, while the algorithm detailed in this invention is based on the linear LS method. The algorithm disclosed here bears similarity to that taught by Roddier et al. in the sense that both algorithms use Gerchberg-type iterations to extrapolate the wavefront outside of the boundary. A basic difference is that Roddier et al. algorithm is based on FFTs instead of the linear LS method.

A difference between the Roddier et al. algorithm and the algorithm of the present invention is the fact that in performing FFTs, the square array matrix satisfies $m=2^q$, and therefore m must be even. In the case of the algorithm of the present invention, there is no such requirement, and odd matrix sizes yield lower error propagation than even matrix sizes.

Without the iterative process, the slope data inside the pupil under test are from wavefront measurements, and the slopes outside of the pupil under test are zero. Therefore, the slope data crossing the original pupil boundaries between $\Omega_0$ and $\Omega_1 \backslash \Omega_0$ are not continuous, and such discontinuous boundary conditions yield severe errors in the reconstructed wavefront not only at the edge of the pupil, but also within the pupil of interest through propagation of errors. In other words, when the slopes do not satisfy the derivative continuity condition of the Poisson equation, deviation errors will be induced.

Figure 5A:
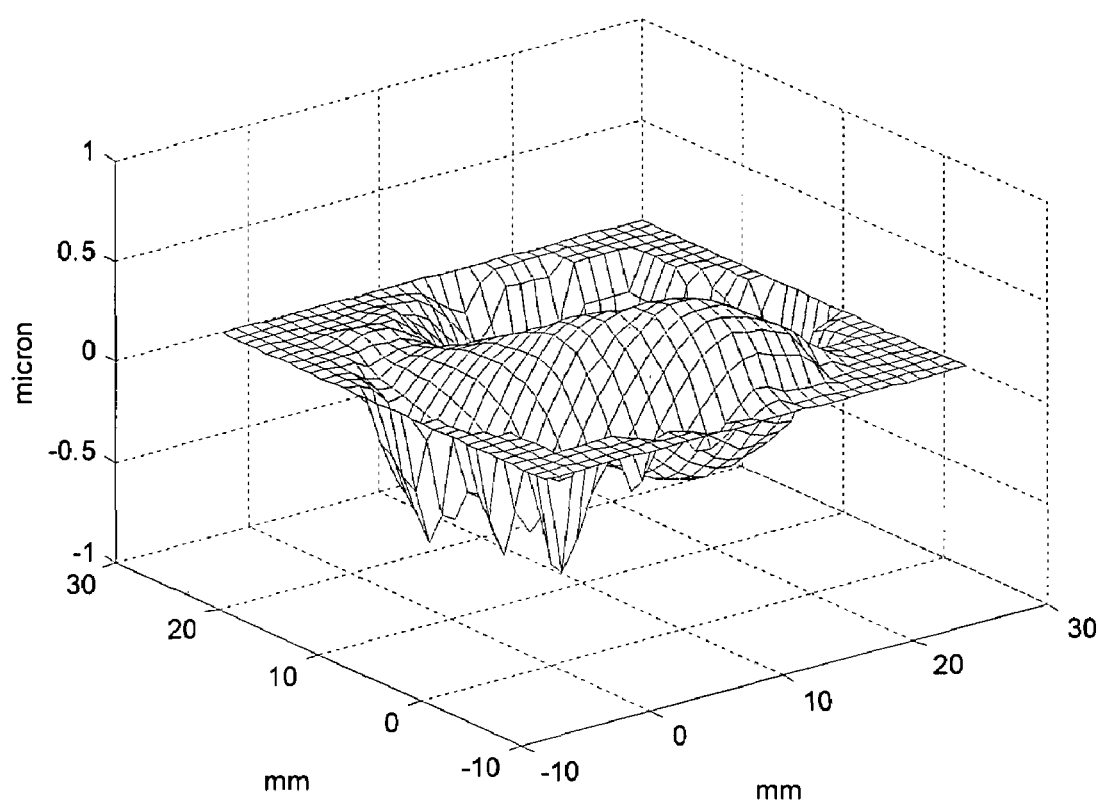
FIG. 5a is an illustration of ground-truth or original wavefront.
Figure 5B:
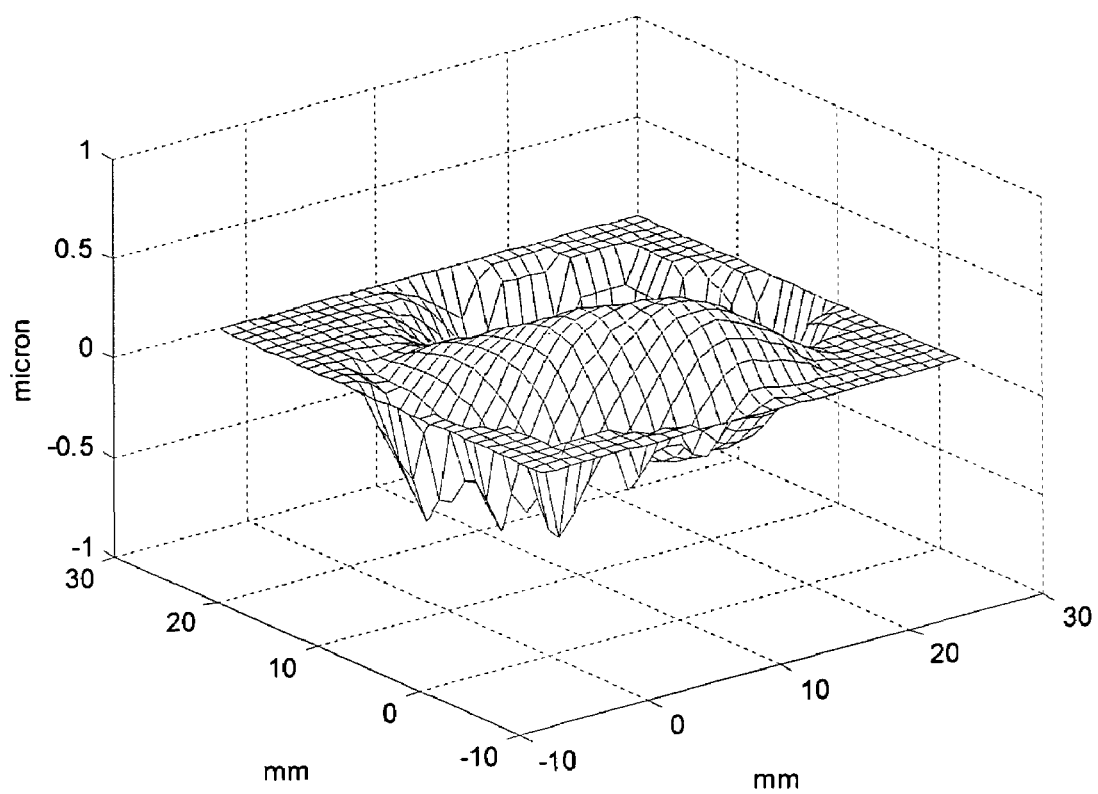
FIG. 5b shows the wavefront reconstructed from measured slope data with the algorithm without iteration.
Figure 5C:
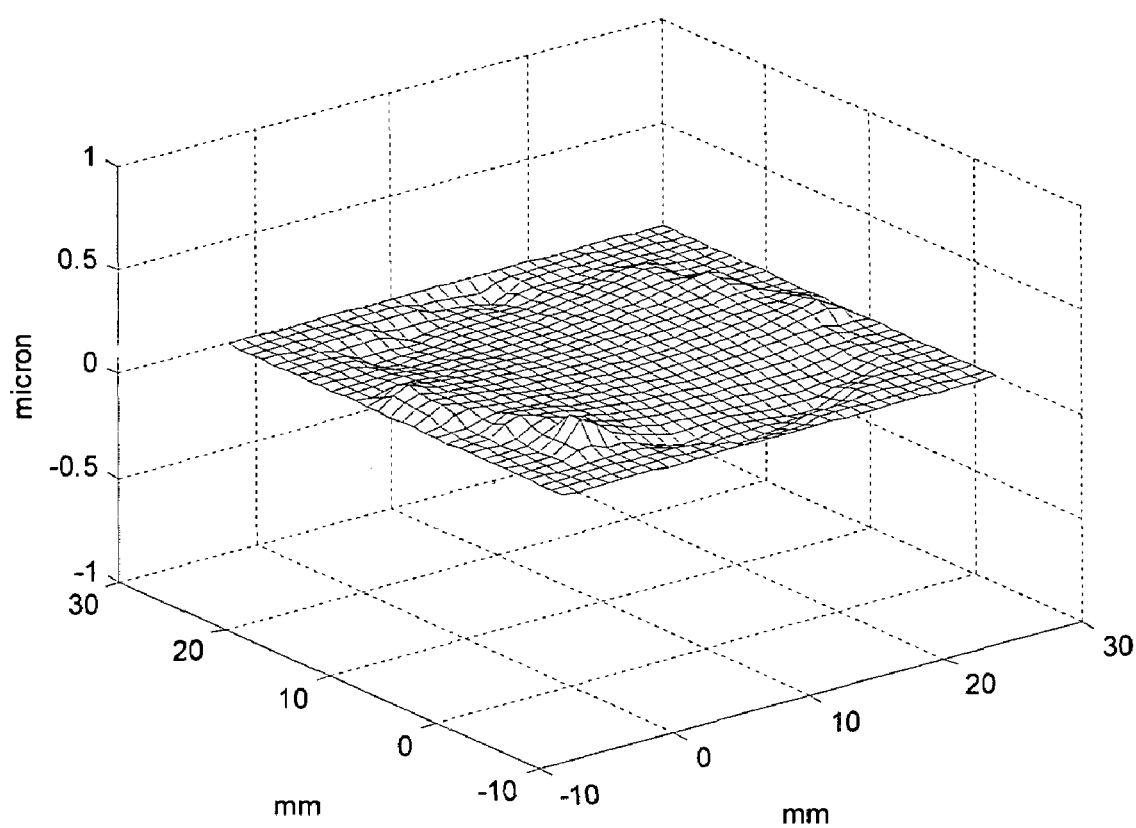
FIG. 5c shows the wavefront deviation error computed as the difference between the ground-truth and the reconstructed wavefront.

FIG. 5a shows an example of an original wavefront (i.e. a reconstructed wavefront which is considered to represent ground truth of wavefront reconstruction as will be further explained below), while the estimated wavefront from slope data without iterations is shown in FIG. 5b.

The differences between the estimated and the original wavefronts represent the deviation errors associated with the domain extension of Zou et al. Therefore, while the domain extension technique is quite useful for developing a universal algorithm, provided that the extended wavefront reconstruction matrix is universal and regular to accommodate irregular pupil shapes and enables efficient computations, the challenge lies in how to establish continuity constraints at the boundaries between $\Omega_0$ and $\Omega_1 \backslash \Omega_0$ to remove the deviation errors in the estimated wavefront.

The iterative process enables a continuous practical extrapolation of the slope data outside of the optical pupil $\Omega_0$, while it does not interfere with the internal region of $\Omega_0$. The iterative algorithm converges quickly to an unbiased solution, while at the same time the smoother the wavefront surface under construction, the smaller the residue deviation error as expected, and the fewer iterations needed. Theoretically, the deviation error of this unique solution will decrease to zero. However, measurement noise prohibits the deviation errors from reaching zero, so they stagger to its minimum.

Sample Results

The gradient-based iterative wavefront estimation algorithm presented in the present invention finds applications to regularly- and irregularly-shaped pupils. In order to validate and assess the capability of the algorithm across irregular shaped pupils, two examples are presented, one with a circular 30-mm diameter pupil, and another with the same size pupil but with a 10% central obstruction. Both data sets were acquired from a previous experiment reported by Zou et al. The 30-mm diameter pupils, with a sampling grid of $2 \times 2$ mm$^2$ element size in both cases, were conjugated to a 500-mm diameter mirror under test. The obstructed wavefront was obtained by considering the slope data within the obstructed pupil only.

In order to establish the ground truth for each set of data, the wavefronts were reconstructed without the domain extension technique from the same set of slope data with the conventional iterative or direct methods, such as the Jacobi iterative method, the Gauss elimination method, and the Cholesky decomposition method.

All these methods yield exactly the same reconstructed wavefront, which is thus considered to represent ground truth (i.e. the original wavefront), against which the proposed iterative wavefront estimation algorithm could be assessed.

Case 1: A Circular Pupil without Central Obstruction

Figure 6A:
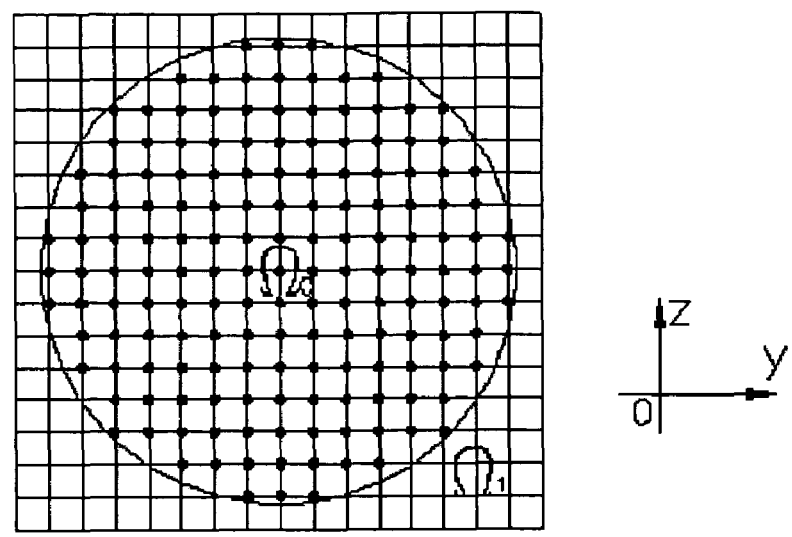
FIG. 6a shows the 30-mm diameter, 2 mm×2 mm sampling grid, circular pupil without central obstruction shown within the extended domain $\Omega_1$.
Figure 6B:
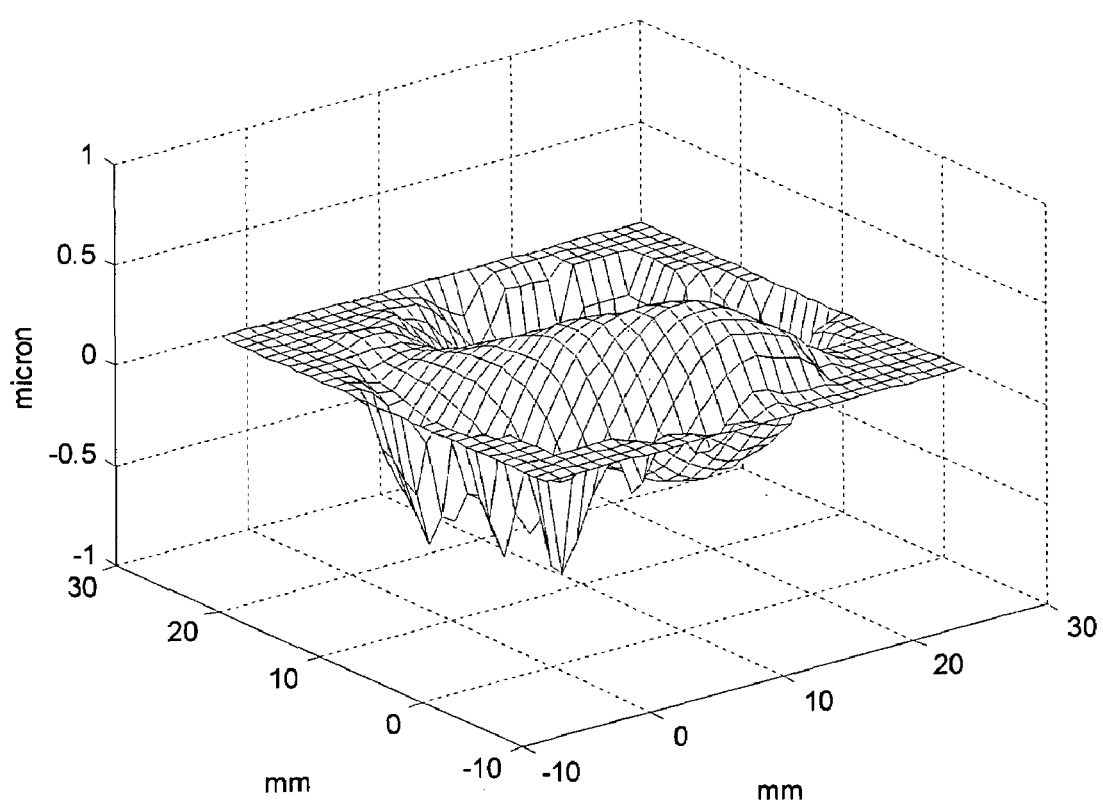
FIG. 6b shows the ground-truth wavefront within the 30-mm diameter circular pupil without central obstruction on a vertical scale of ±1 μm.
Figure 7A:
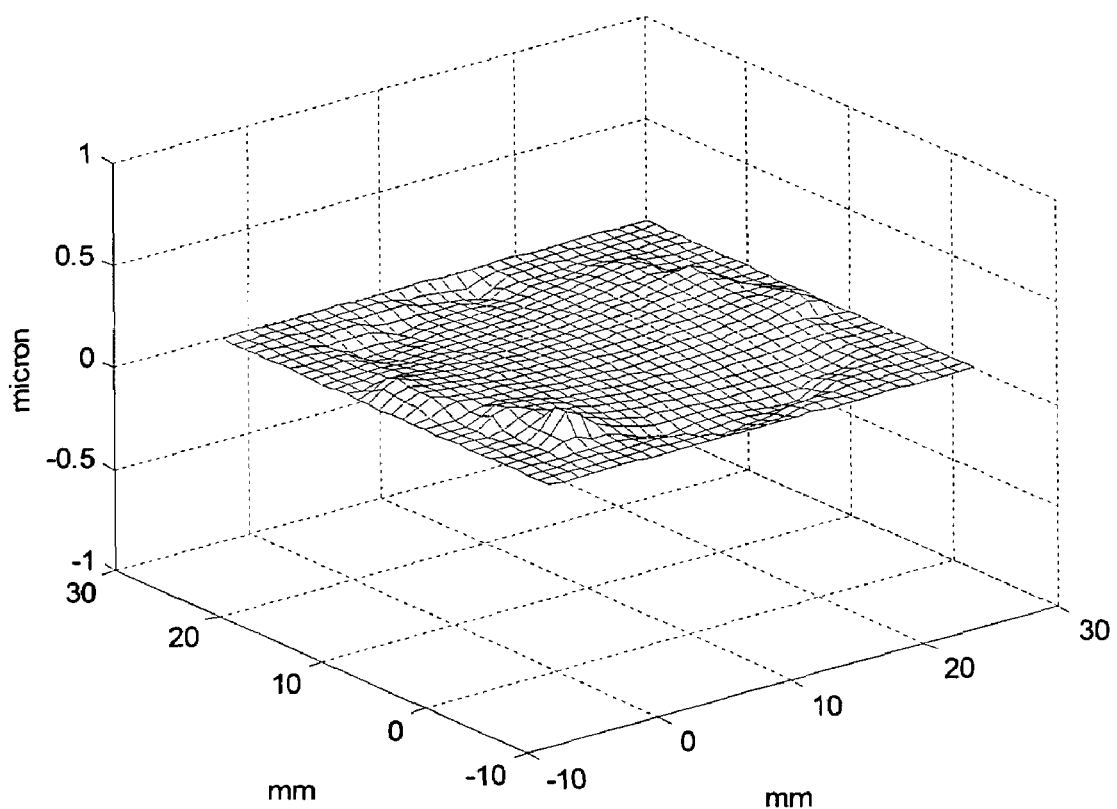
FIG. 7a shows the wavefront deviation error (on a vertical scale of ±1 μm) for a 30 mm diameter circular pupil without obstruction across a sampled 15×15 points grid for no iterations and for $\lambda=632.8$ nm.
Figure 7B:
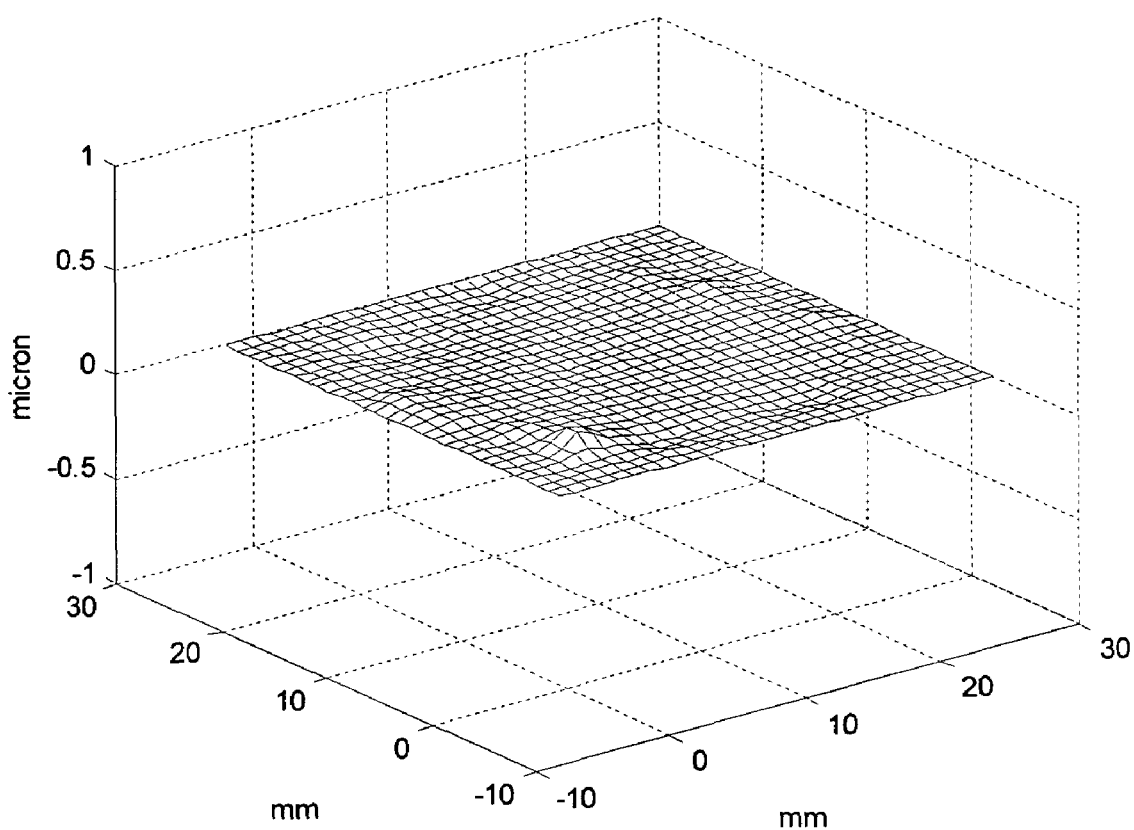
FIG. 7b shows the wavefront deviation error (on a vertical scale of ±1 μm) for a 30 mm diameter circular pupil without obstruction across a sampled 15×15 points grid after 1 iteration and for $\lambda=632.8$ nm.
Figure 7C:
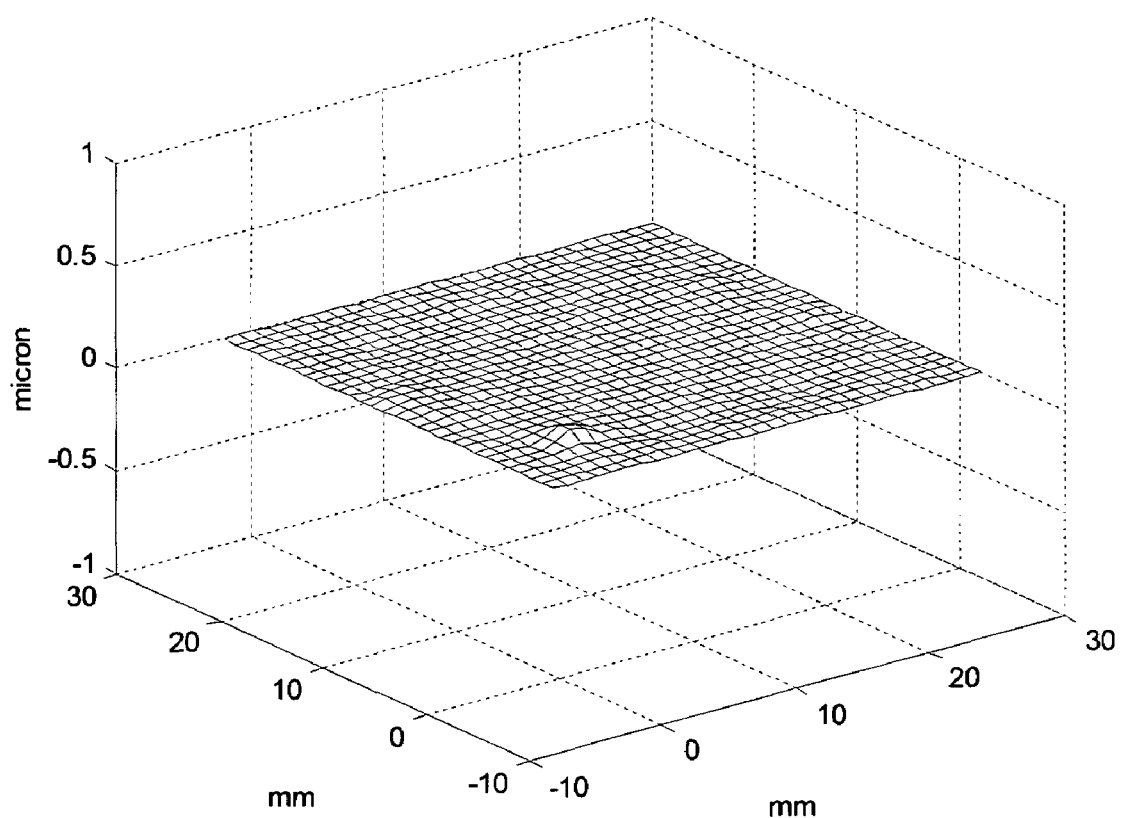
FIG. 7c shows the wavefront deviation error (on a vertical scale of ±1 μm) for a 30 mm diameter circular pupil without obstruction across a sampled 15×15 points grid after 2 iterations and for $\lambda=632.8$ nm.
Figure 7D:
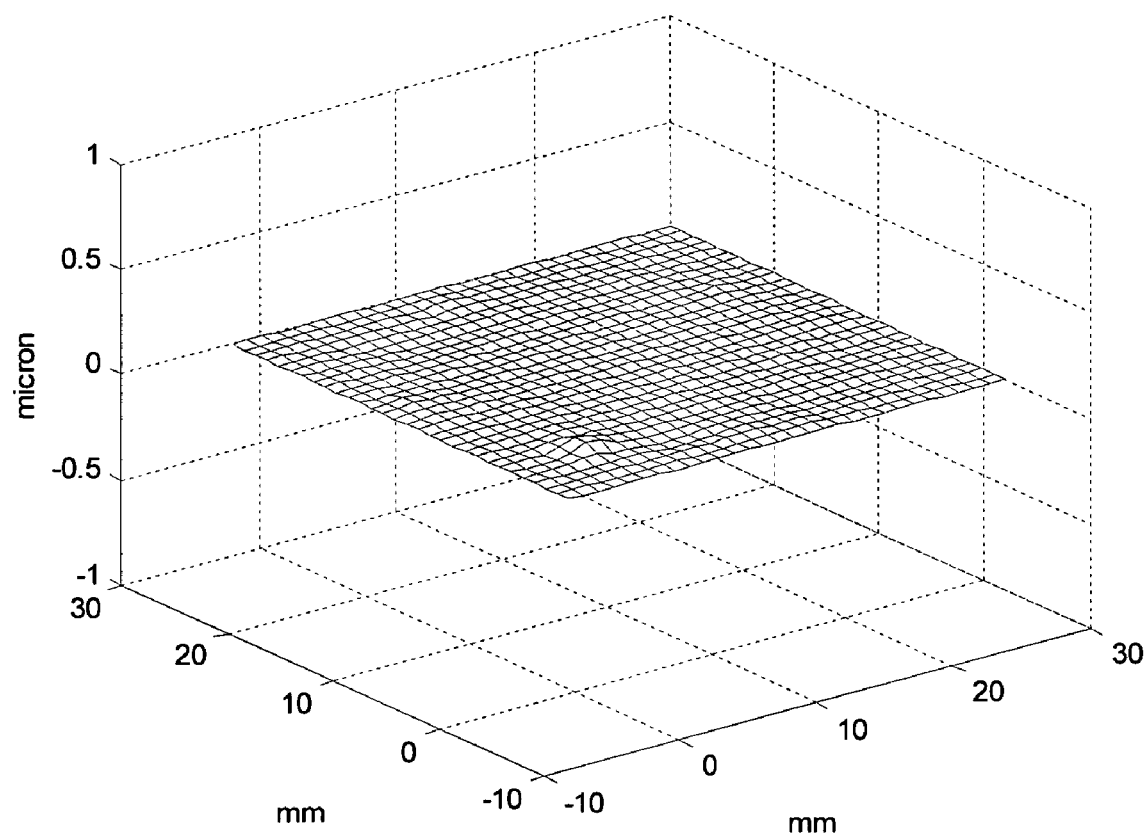
FIG. 7d shows the wavefront deviation error (on a vertical scale of ±1 μm) for a 30 mm diameter circular pupil without obstruction across a sampled 15×15 points grid after 3 iterations and for $\lambda=632.8$ nm.
Figure 7E:
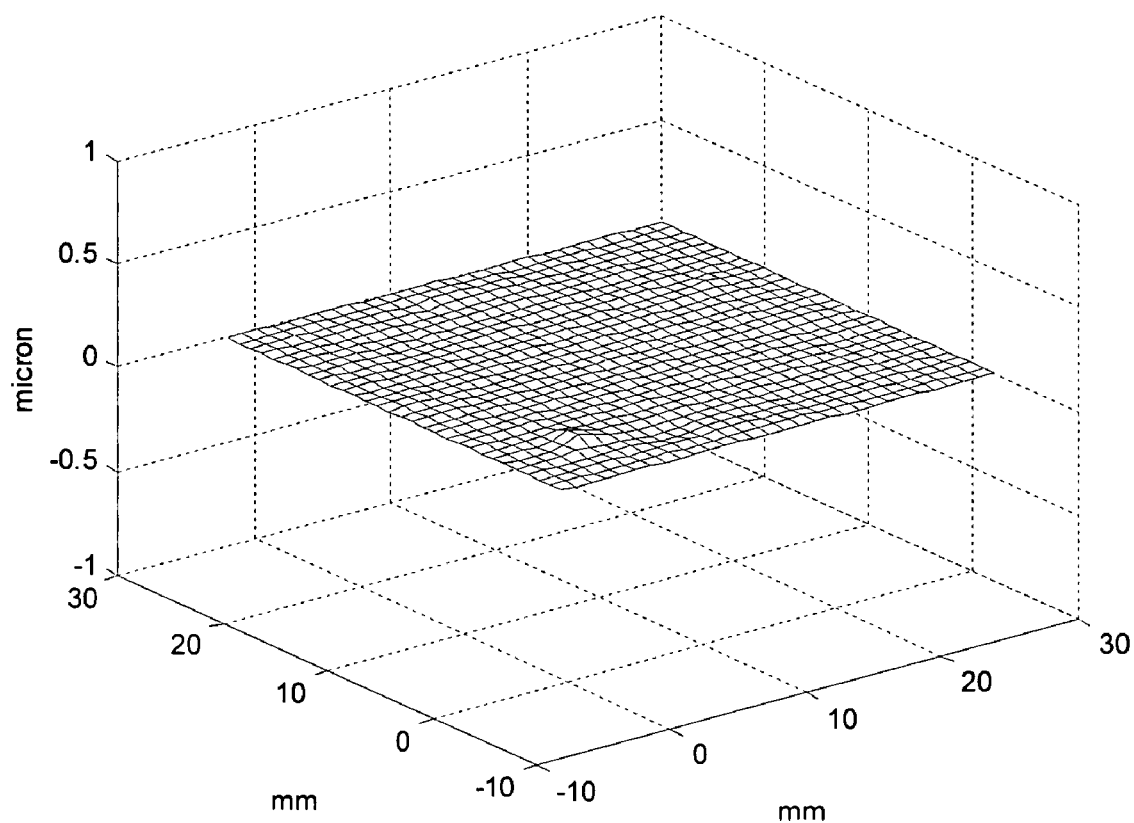
FIG. 7e shows the wavefront deviation error (on a vertical scale of ±1 μm) for a 30 mm diameter circular pupil without obstruction across a sampled 15×15 points grid after 4 iterations and for $\lambda=632.8$ nm.
Figure 7F:
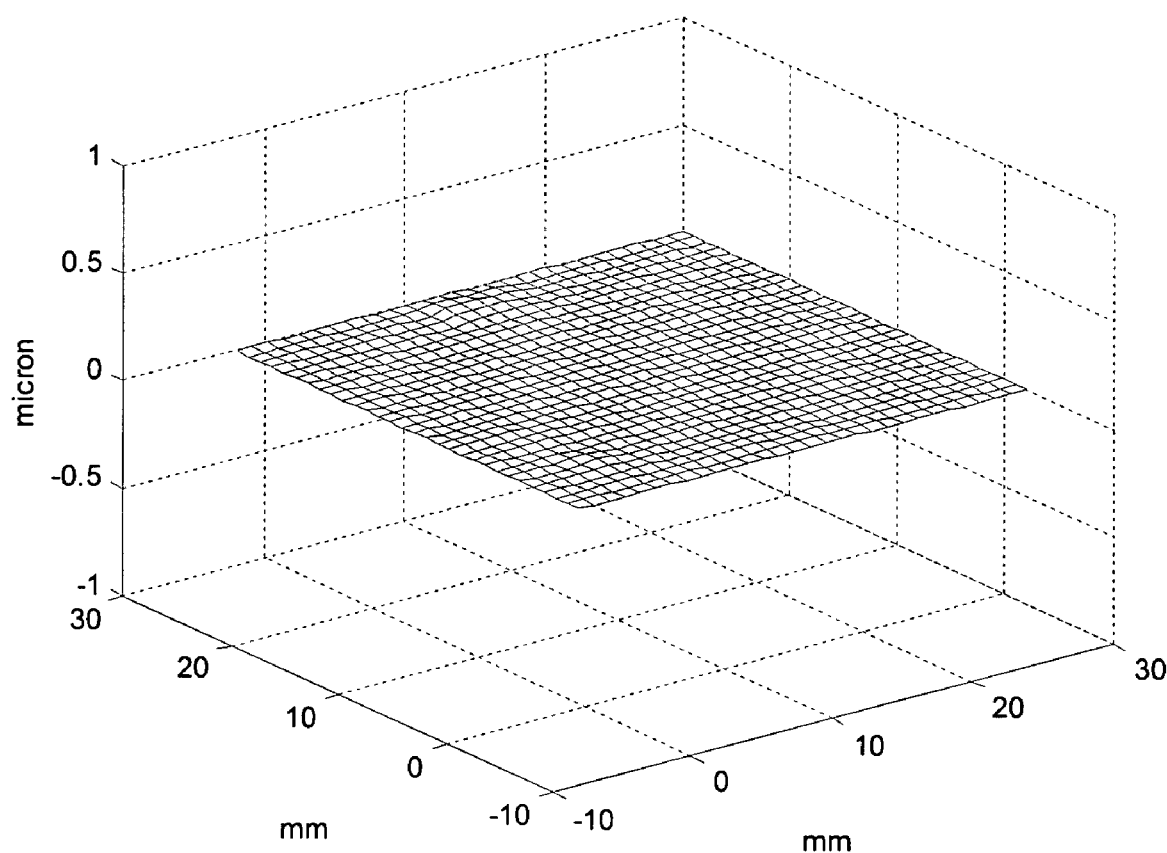
FIG. 7f shows the wavefront deviation error (on a vertical scale of ±1 μm) for a 30 mm diameter circular pupil without obstruction across a sampled 15×15 points grid after 13 iterations and for $\lambda=632.8$ nm.

A circular pupil without obstruction is a simply connected domain. The considered 30-mm diameter pupil with an array of 161 Shack-Hartmann grid points is shown in FIG. 6a. The points outside of the circular pupil in the square lattice are the imaginary grid points. The ground-truth wavefront is also shown in FIG. 6b. Deviation-error maps of the wavefront reconstructed by the Gerchberg-type iterative algorithm with several numbers of iterations (i.e. i=0, 1, 2, 3, 4, 13) are shown in FIGS. 7a–7f. Results show that for $\lambda$=632.8 nm, the RMS deviation errors were reduced from $\lambda/16$ to $\lambda/129$ after 13 iterations, where it reached its minimum.

Case 2: A Circular Pupil with a 10% Central Obstruction

Figure 8A:
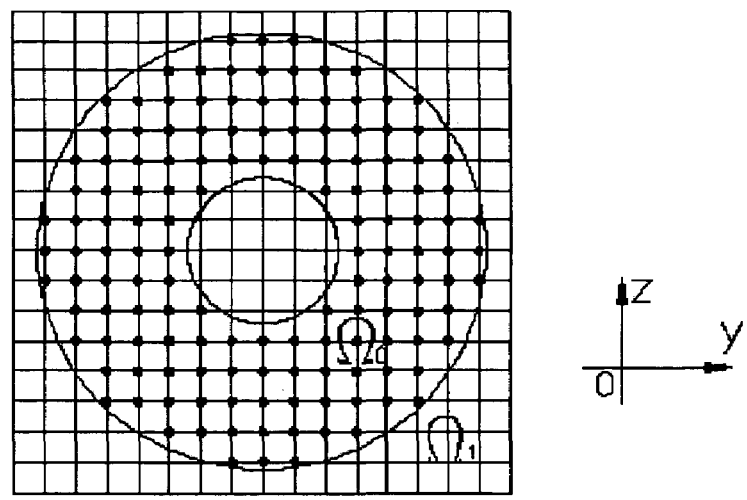
FIG. 8a shows a 30-mm diameter circular pupil with a 10% central obstruction.
Figure 8B:
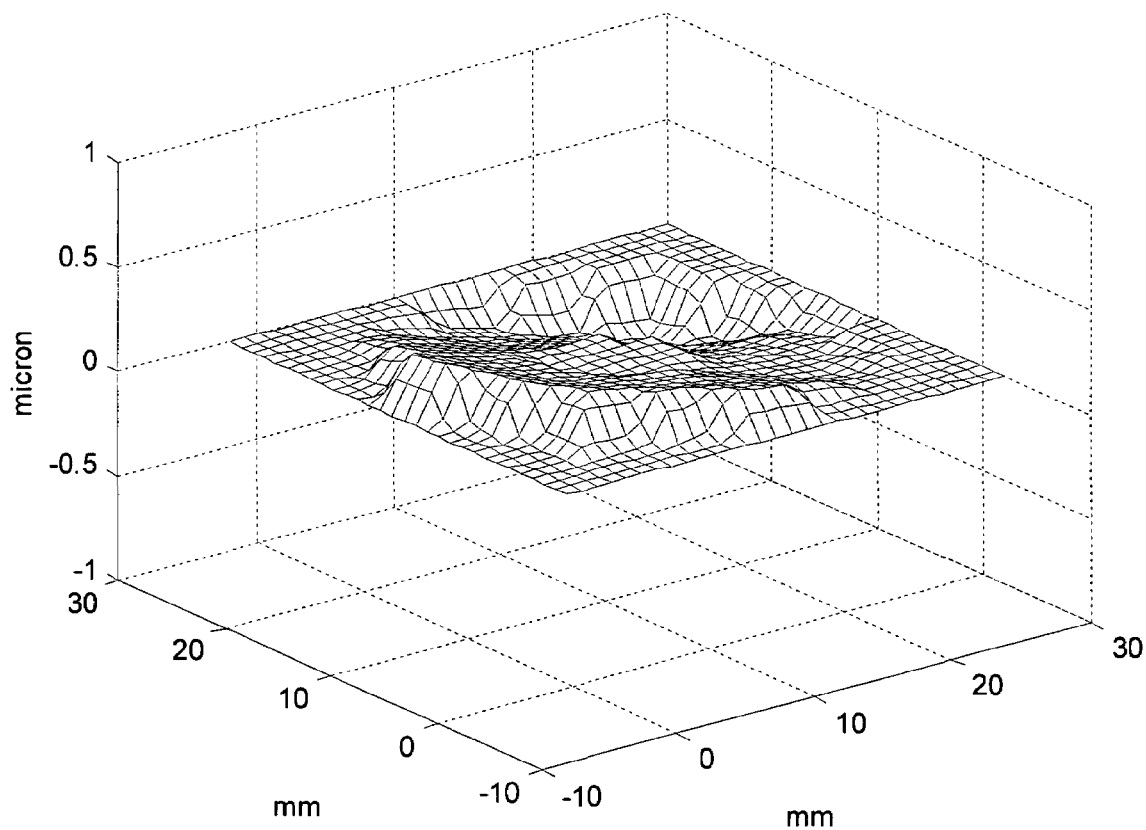
FIG. 8b shows the ground-truth wavefront for a 30-mm diameter circular pupil with a 10% central obstruction on a vertical scale of ±1 μm.
Figure 9A:
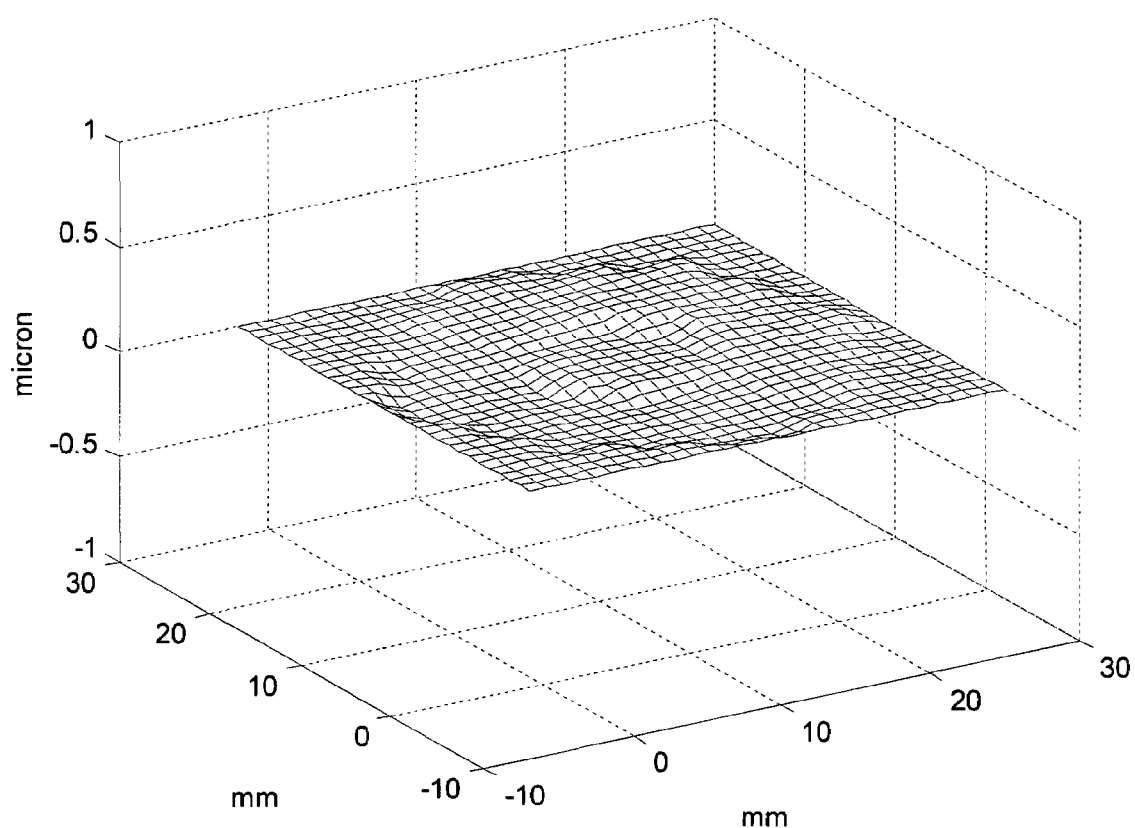
FIG. 9a shows the wavefront deviation error (on a vertical scale of ±1 μm) for a 30 mm diameter circular pupil without obstruction across a sampled 15×15 points grid, with a 10% central obstruction, for no iterations and for λ=632.8 nmn.
Figure 9B:
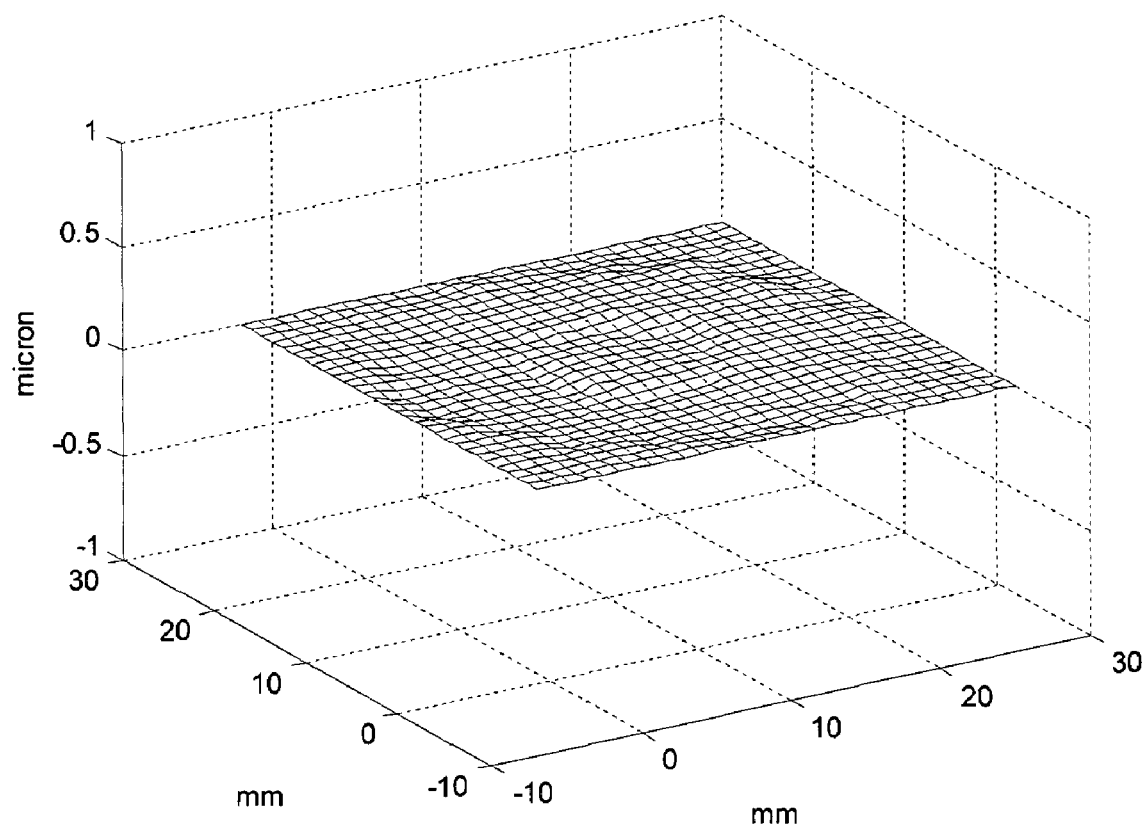
FIG. 9b shows the wavefront deviation error (on a vertical scale of ±1 μm) for a 30 mm diameter circular pupil without obstruction across a sampled 15×15 points grid, with a 10% central obstruction, after 1 iteration and for λ=632.8 nm.
Figure 9C:
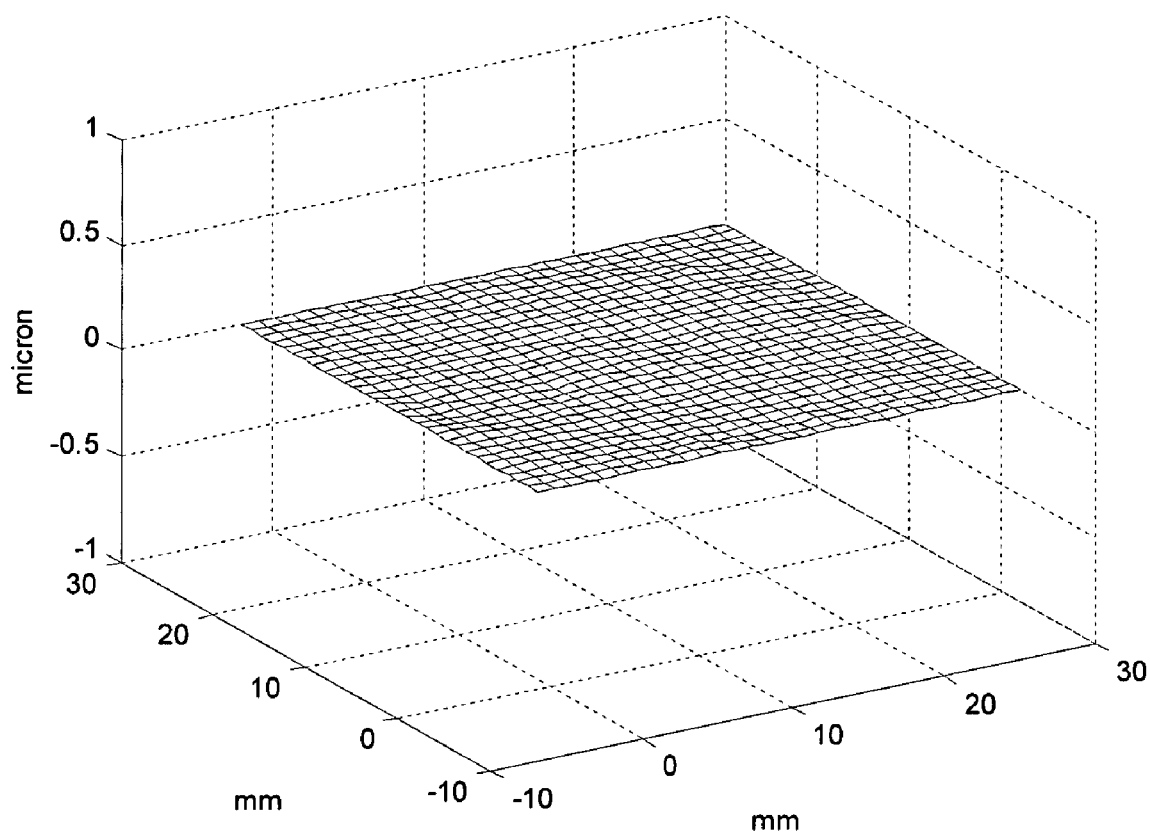
FIG. 9c shows the wavefront deviation error (on a vertical scale of ±1 μm) for a 30 mm diameter circular pupil without obstruction across a sampled 15×15 points grid, with a 10% central obstruction, after 2 iterations and for λ=632.8 mm.
Figure 9D:
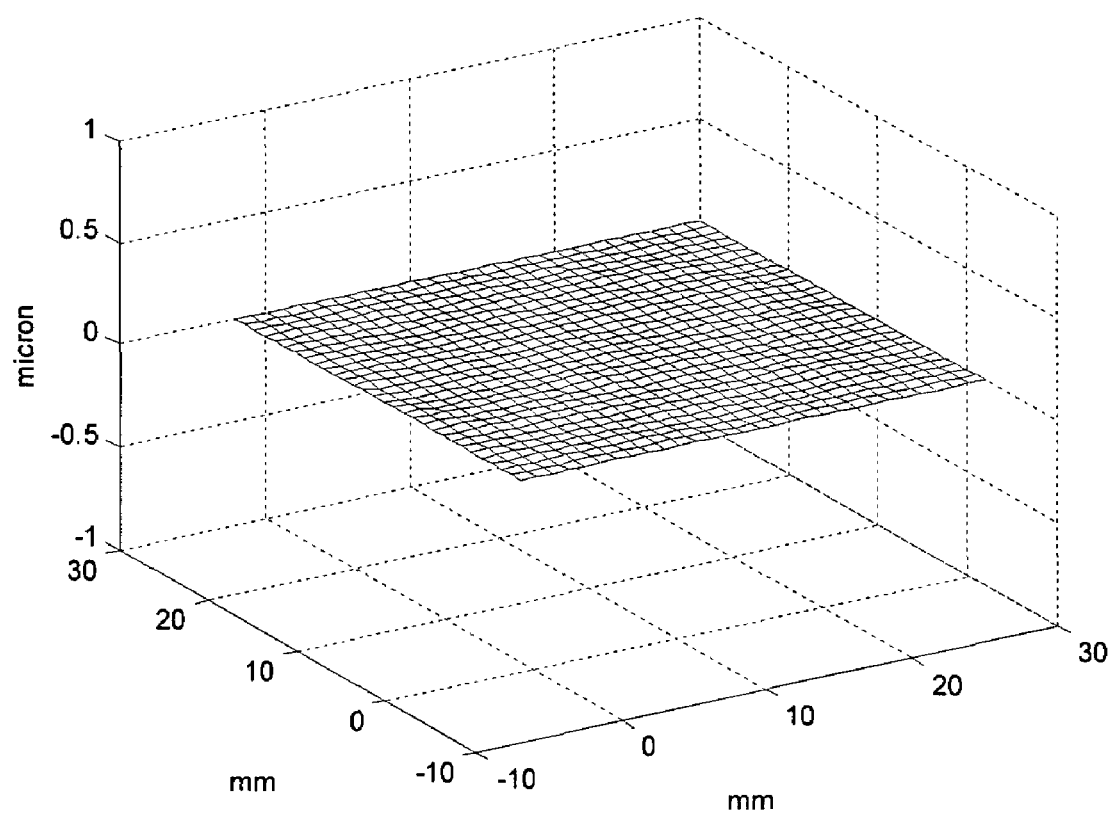
FIG. 9d shows the wavefront deviation error (on a vertical scale of ±1 μm) for a 30 mm diameter circular pupil without obstruction across a sampled 15×15 points grid, with a 10% central obstruction, after 3 iterations and for λ=632.8 nm.
Figure 9E:
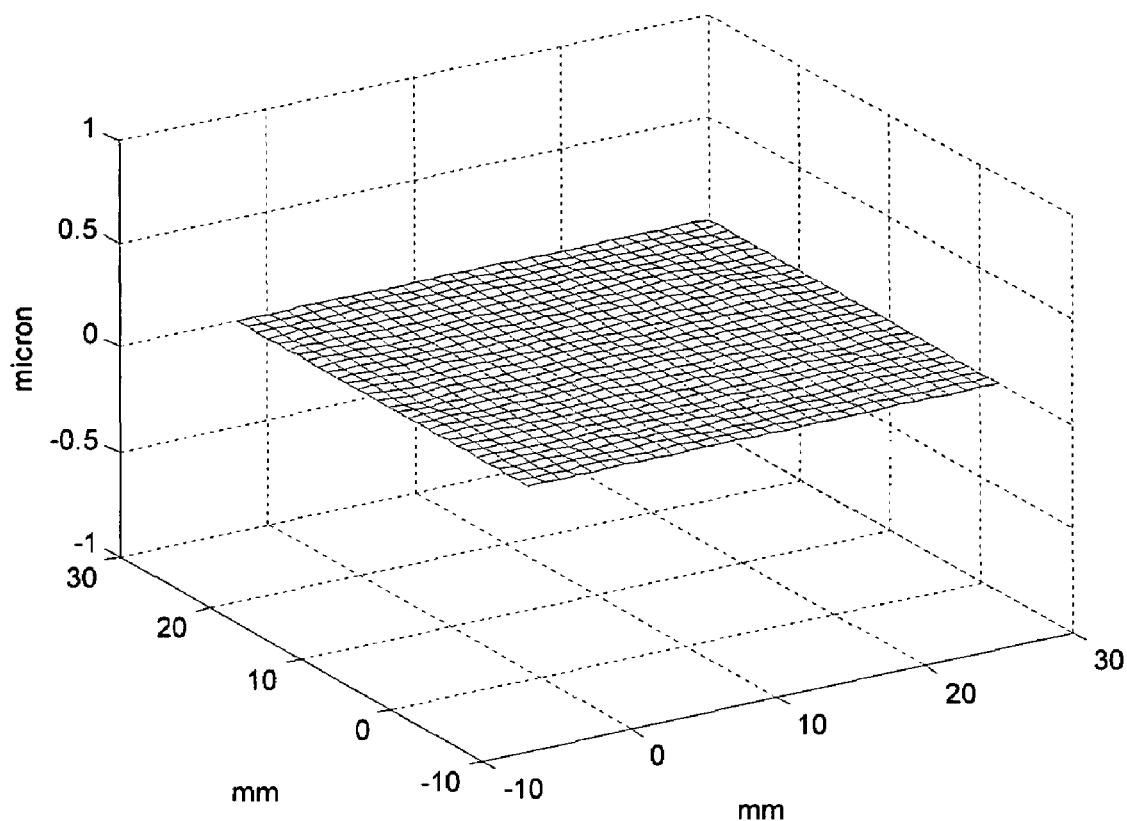
FIG. 9e shows the wavefront deviation error (on a vertical scale of ±1 μm) for a 30 mm diameter circular pupil without obstruction across a sampled 15×15 points grid, with a 10% central obstruction, after 4 iterations and for λ=632.8 nm.
Figure 9F:
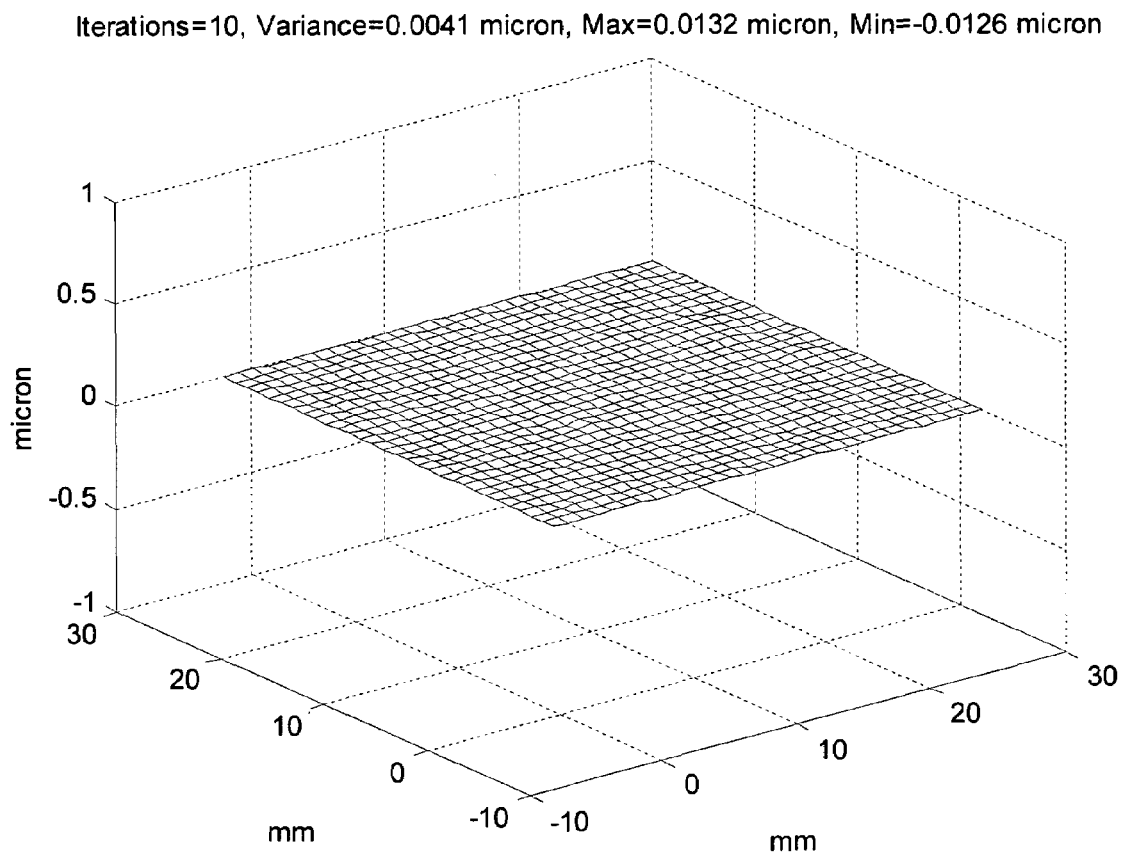
FIG. 9f shows the wavefront deviation error (on a vertical scale of ±1 μm) for a 30 mm diameter circular pupil without obstruction across a sampled 15×15 points grid, with a 10% central obstruction, after 10 iterations and for λ=632.8 nm.

The 30-mm circular pupil with a 10% central obstruction is shown in FIG. 8a. Such a percent of obscuration is common for astronomical telescope mirrors. In testing such mirrors during the fabrication process and telescope assembling, an algorithm that enables testing of any pupil shape without any additional steps in preparing and setting-up for such test provides key advantages not only in time efficiency but also in minimizing the risk of test-induced errors. The ground-truth wavefront is shown in FIG. 8b.

Deviation-error maps of the wavefronts reconstructed by the Gerchberg-type iterative algorithm with several numbers of iterations (i.e. i=0, 1, 2, 3, 4, 10) are shown in FIGS. 9a–9f. Results show that for $\lambda$=632.8 nm, the RMS deviation errors were reduced from $\lambda/14$ to $\lambda/154$ after 10 iterations, where it reached its minimum.

Figure 10:
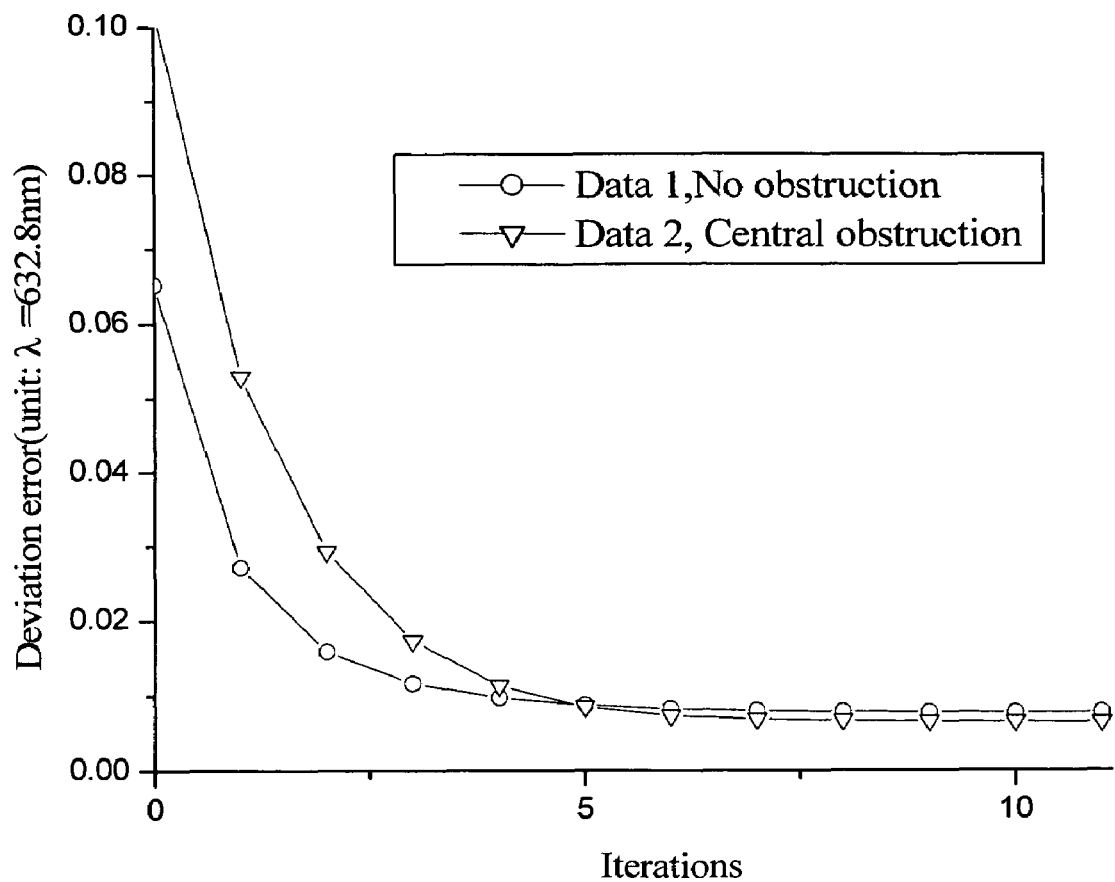
FIG. 10 shows a plot of RMS deviation errors in units of wavelength as a function of the number of iterations for the two data sets considered.

The algorithmic convergence for the present invention is superior to the prior arts. The deviation error reduction through Gerchberg-type iterations was found to be efficient. Specifically, the final deviation errors after a maximum of 5 iterations for the two examples considered were less than $\lambda/100$ for $\lambda$ equal to 632.8 nm, as shown in FIGS. 7a–7f and FIGS. 9a–9f. The convergence indicated by the RMS wavefront error in units of wavelength as a function of the number of iterations is plotted in FIG. 10 for the two case datasets presented above. Such a finding is high performance for optical testing, and the algorithm can be said to be very efficient.

A theoretical analysis of the computational complexity of the present invention reveals that the algorithm is efficient. In this iterative wavefront reconstruction algorithm, there are three m×m (note that m=t×t) linear equation sets that need to be solved at each iteration. One is the equation set for wavefront reconstruction from the slope data, and the two others are the equation sets for y-slope and z-slope computations from a known wavefront. The three equation sets are highly sparse.

If a fill-in factor is defined, an indicator of matrix sparsity, as the quotient of the number of nonzero elements to the total number of the matrix elements, then the fill-in factor of the wavefront reconstruction matrix $C^T C$ is $(5t-4)/t^3$, and the fill-in factors of the slope computation matrices $A^T A$ and $B^T B$ are both $(t+4)/t^3$. For example, the fill-in factors of the wavefront reconstruction matrix and the slope computation matrices are 4.6% and 1.4% respectively for t=10, and they decrease to 0.05% and 0.01% at t=100.

Spatial complexity of the linear least-squares-based solution is examined. Besides their high sparsity, all three matrices are symmetrical, positive and banded, once the wavefront zero-point has been determined for the wavefront reconstruction. The extremely regular and symmetrical banded matrices allow efficient computations in solving linear equation sets because the nonzero elements in these matrices are regularly patterned with the numbers 4,3,2,1,−1 only. Therefore, the matrix storage problem is avoided in this algorithm except for about $t^3$ elements space reserved for the banded Cholesky decomposition of $C^T C$, which is a much smaller part in comparison to the $t^{4/2}$ element space set for a conventional Cholesky decomposition. Naturally, a space of $3t^2$ elements is necessary in each algorithm for storing the slope data and the wavefront values.

Before discussion of the computational complexity of the linear least-squares-based solution of the algorithm of the present invention, the term "FLOPS" (Floating-Point Operations) will be introduced to denote the arithmetic operations that a computer performs, such as multiplications, additions, or the like.

The positive definite slope-extraction matrices $A^T A$ and $B^T B$ are banded and diagonal with semi-bandwidths of 2 and t, respectively. In computing slope data from a wavefront, it is an advantage to employ a direct solution method such as the Cholesky method to solve the normal equation sets because the matrices $A^T A$ and $B^T B$ can be decomposed into two unique triangular matrices by simple derivations once and for all. Thereby no more Cholesky decompositions are needed in computation. The computations needed in solving the two systems of equations are substitutions only, which need arithmetic costs of about 4m times the bandwidth, which yields $8t^2$ FLOPS for $A^T A$ and $4t^3$ FLOPS for $B^T B$. As a comparison, the computational cost needed for substitutions in solving an equation without exploiting the band structure is $2t^4$ FLOPS.

To solve the linear system of equations for wavefront reconstruction, the zero-point for the wavefront under construction is set to make the matrix $C^T C$ positive definite before the Cholesky decomposition is performed. Since it is a banded sparse matrix with a semi-bandwidth of t, this equation set can be solved by a banded Cholesky decomposition method, which needs about $t^4$ FLOPS for decomposition and $4t^3$ FLOPS for substitutions. As a comparison, employing the conventional Cholesky method to solve this equation set without exploiting the band structure of the matrix yields approximately $$\frac{1}{3}t^6 + 2t^4$$

FLOPS.

Other direct solution methods are also available in solving the above three equation sets, such as the Gaussian Elimination and the Singular Value Decomposition (SVD) methods, but such methods are more computationally expensive. Generally, the conventional Gaussian Elimination method needs about $$\frac{2}{3}t^6$$

FLOPS, and the SVD method needs about $12t^6$ FLOPS. Because the SVD method yields a unique solution with minimum-norm for a rank deficient least squares problem, it is a good method in practice if the computational complexity is not a constraint.

An alternative to solve linear systems is to use iterative methods, such as the Successive Over-Relaxation (SOR) algorithm, which is said to be one of most efficient among the classical iterative methods. The convergence rate of the SOR method is closely related to the problem model, the discretization mesh size, the relaxation factor and the grid indexing orders. However, the iteration counts needed for the optimal SOR method to converge to a solution within a precision of $10^{-8}$ can be estimated by $$R_{\omega b} = -8\left(\log_{10}\left(1 - \frac{2\pi}{t-1}\right)\right)^{-1} \approx 2.94(t+1) \approx 3t \qquad (37)$$

If approximately $5t^2$ FLOPS operations are required for each iteration, then the computational cost needed for solving Equation (7) with the optimal SOR method is approximately $15t^3$ FLOPS. The analysis indicates that the banded Cholesky method needs less FLOPS of computational cost for a small grid size (t<11), but for a large grid size the SOR method is computationally less expensive. The complexity of the optimal SOR method increases with a cubic curve, whereas the complexity of banded Cholesky method increases with a quadratic curve.

The complexity of the present invention is now compared with the complexity of FFT-based iterative algorithms. The fast Fourier transform (FFT) of a data set of length $m=2^q$ (q is a positive integer) requires about $m \log_2 (m)$ complex multiplications, which is equivalent to $5m \log_2 (m)$ FLOPS of arithmetic operations according to a detailed analysis by Brigham ("The fast Fourier transform and its applications", p134, p164, Prentice Hall, Englewood Cliffs, N.J., 1988). The FFT-based iterative algorithm proposed by Roddier et al. needs to compute two FFTs besides the computations of the y- and the z-slopes from the wavefront at each iteration. Therefore, if the computation of the slope extractions takes the same computational cost in both algorithms and this cost is ignored, the computational cost needed in one iteration of FFT-based iterative algorithm is approximately $(20 \log^2(t) + 7)t^2$ FLOPS, which is usually much smaller than that of the optimal SOR-based (i.e. $15t^3$ FLOPS) iterative algorithm.

Thus based on computational complexity evaluation, the FFT-based algorithm is superior in performance to the algorithm of the present invention, which could be significant for large values of grid-array size t (t×t=m). Also, the required number of iterations for each algorithm will significantly affect the overall computational time. The number of iterations is a factor of the overall grid-array size, measurement noise levels, and such. The FFT-based algorithms usually converge slowly; for example, the Gerchberg-Saxton algorithm needs at least tens to hundreds or even thousands of iterations to converge to a solution, while the algorithm of the present invention converges to less than $\lambda/100$ deviation error after a maximum of approximately five iterations.

It has been established that the space complexity required for a Fast Fourier Transform (FFT) is approximately $O(t^4)$, which corresponds to the storage of complex matrix arrays. For the Gerchberg-type iterative algorithm of the present invention with banded Cholesky solution method, the spatial complexity is only approximately $O(t^3)$.

The error propagation coefficient of the present invention is slow as compared to the prior art. If the perturbations introduced by the rounding errors are neglected, wavefront errors may occur from two sources: the algorithm discretization errors that depend on the basic reconstruction scheme adopted, and the wavefront sensor measurement error, such as the CCD centroiding. The discretization errors of the wavefront reconstruction scheme adopted by this invention have been discussed by Zou et al.

The error propagation of the wavefront reconstruction from the wavefront measurements is now considered. For convenience of comparison, the noise coefficient is defined as taught by Southwell. A universal wavefront reconstruction matrix C is assumed. The wavefront slope measurement error vector may be given as $S'=(s'_1 \ s'_2 \ \ldots \ s'_m)^T$, and the wavefront error vector may be expressed as $W'=(w'_1 \ w'_2 \ \ldots \ w'_m)^T$. If the algorithm discretization errors are ignored, the error propagation matrix equation can be written as $$C^T C W' = a C^T S' \tag{38}$$

where C was defined in Equation (5), and a is the distance between grid points. The Euclidian norm of vector X is introduced as $$\|X\|_2 = (X^T X)^{1/2}, \tag{39}$$

and the corresponding matrix norm for a matrix C as $$lub_2(C) = \max_{X \neq 0} \left( \frac{X^T C^T C X}{X^T X} \right)^{1/2} = [\rho(C^T C)]^{1/2}, \tag{40}$$

where $\rho(C^T C)$ is the spectral radius of $C^T C$. If $C^T C$ is invertible, then $$\|W'\|_2 \leq a \frac{[cond(C^T C)]^{1/2}}{lub_2(C)} \|S'\|_2 \tag{41}$$

where $cond(C^T C)$ is defined as the matrix condition number of $C^T C$, and $$cond(C^T C) := lub_2(C^T C) \, lub_2[(C^T C)^{-1}] = \rho(C^T C) \rho [(C^T C)^{-1}]. \tag{42}$$

Since $\rho(C^T C) = |\lambda_{max}|$, then $\rho[(C^T C)^{-1}] = |\lambda_{min}|^{-1}$, where $\lambda_{max}$ and $\lambda_{min}$ are the maximum and minimum of the eigenvalues of matrix $C^T C$, respectively. Therefore the condition number of $C^T C$ can be written as $$cond(C^T C) = \frac{|\lambda_{max}|}{|\lambda_{min}|}. \tag{43}$$

Then Equation (41) becomes $$\|W'\|_2 \leq \frac{a\|S'\|_2}{\sqrt{|\lambda_{min}|}}. \tag{44}$$

If the wavefront slope errors are independent and have the same variance $\sigma_s^2$, then consider $$\|W'\|_2 = \sqrt{m} \left( \frac{1}{m} \sum_{i=1}^{m} |w'_i|^2 \right)^{1/2} = t\sigma_w, \tag{45}$$

and $$\|S'\|_2 = \sqrt{m} \left( \frac{1}{m} \sum_{i=1}^{m} |s'_i|^2 \right)^{1/2} = t\sigma_s, \tag{46}$$

where $\sigma_w$ and $\sigma_s$ are the rms errors of the wavefront and the wavefront slope measurements, respectively. According to Equations (44)–(46)

$$\sigma_w \le \frac{a\sigma_s}{|\lambda_{\min}|^{1/2}}. \tag{47}$$

Letting $\sigma_d$ be the rms error of the wavefront difference measurements with $\sigma_d = a\sigma_s$, then $$\sigma_w \le \gamma \sigma_d, \tag{48}$$

where $$\gamma = |\lambda_{\min}|^{-1/2}. \tag{49}$$

It is a limit estimation of error propagation coefficients, where $\gamma^2$ is the limit ratio of the mean square of wavefront error to the mean square of the wavefront difference error, which is called the noise coefficient or error propagation coefficient, where $$\sigma_w^2/\sigma_d^2 \le \gamma^2 = |\lambda_{\min}|^{-1}. \tag{50}$$

Equation (50) points to the well-known fact that the error propagation coefficient is limited by the reciprocal of the minimum eigenvalue of the normal matrix.

The analysis is also applicable to the error propagation of slope computation provided by Equations (22) and (36). The problem is then reduced to evaluating the minimum eigenvalue of the normal matrix. Since the normal equation matrix is symmetric, the classical Jacobi method can be employed to compute the eigenvalues. The eigenvalues of the two slope-computation matrices of Equations (22) and (36) are found to be $2-\sqrt{2}$, $2+\sqrt{2}$ and 4 when t>4; for t=4, the eigenvalues are $2-\sqrt{2}$ and $2+\sqrt{2}$ only. Thereby the condition numbers of these two matrices are both $4/(2-\sqrt{2}) \approx 6.83$, except for t=4 at which value the condition number is $((2+\sqrt{2})/(2-\sqrt{2}) \approx 5.83$. Therefore for y- (or equivalently z-) slope computations $$\sigma_s^2/\sigma_w^2 \le \frac{1}{2-\sqrt{2}} = 1 + \frac{\sqrt{2}}{2} \approx 1.71 \quad t \ge 4 \tag{51}$$

Figure 11:
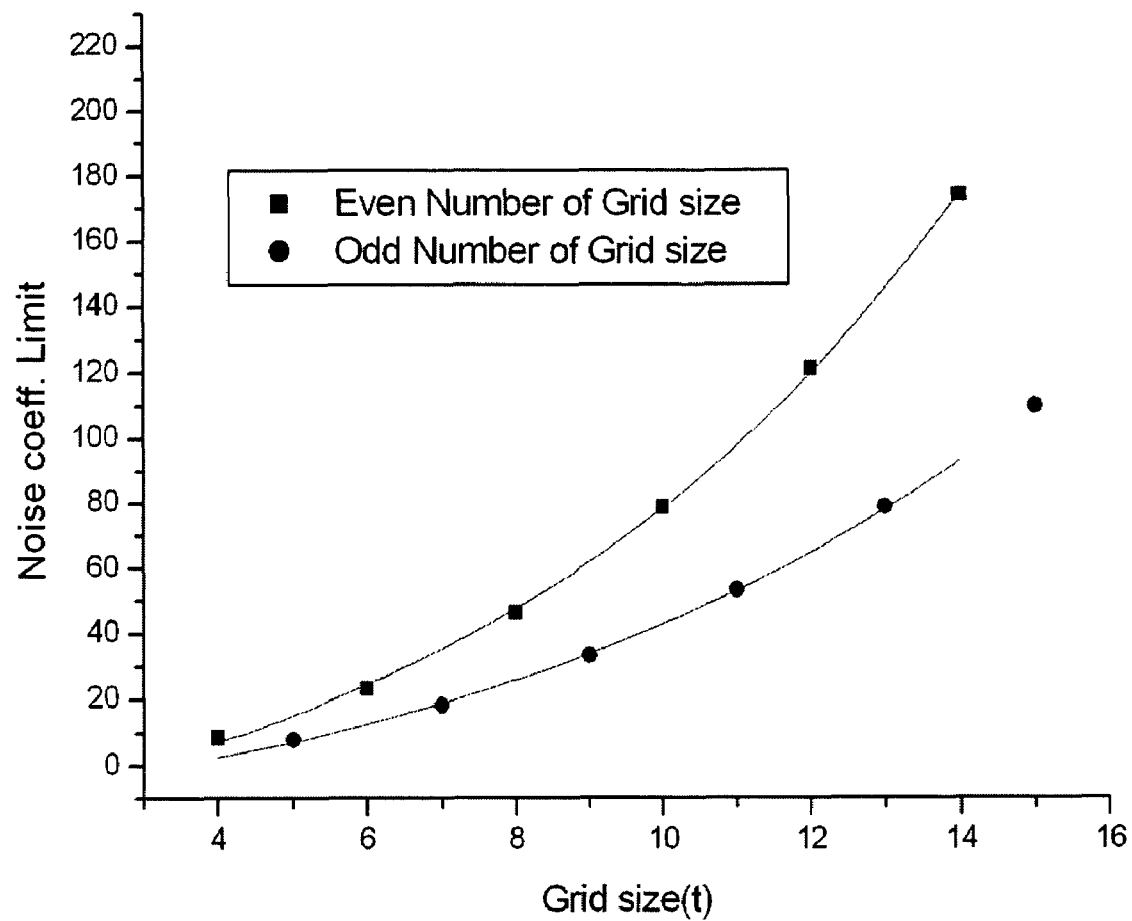
FIG. 11 shows the noise coefficient limit versus the dimension size of the sampling grid.

For the wavefront reconstruction matrix in Equation (7), the situation is more complex because the eigenvalues of this matrix are sensitive to the variation of the wavefront zero-point, the matrix dimension size, and even the parity of the number of the matrix dimension. Employing the classical Jacobi method to compute the eigenvalues of Equation (7), the curve of the noise coefficient limit versus the grid size of the wavefront is obtained and shown in FIG. 11.

Results show that the wavefront reconstruction has a better performance in error propagation when the number of the reconstruction matrix dimension is odd. Therefore, an odd number of the sampling grid array is preferable to its closest even number of the sampling grid array. Making a least square fitting of this curve, the relationship can be expressed quantitatively as $$\sigma_w^2/\sigma_d^2 \le \gamma^2 = \begin{cases} -44 + 28.577 e^{\frac{t}{8.925}}, & t \text{ is even} \\ -31.875 + 20.607 e^{\frac{t}{7.766}}, & t \text{ is odd} \end{cases} \tag{52}$$

Figure 12:
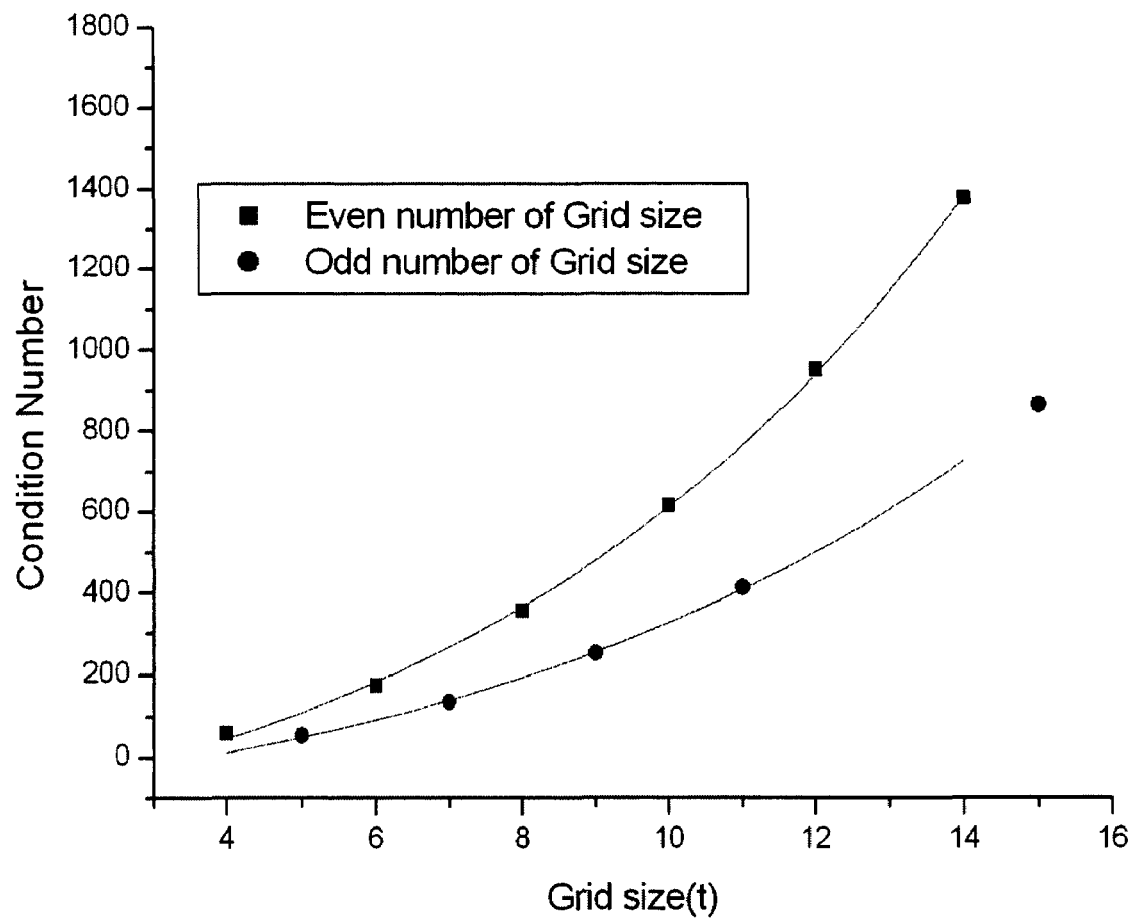
FIG. 12 shows the normal matrix condition number versus grid dimension size.

The error propagation of parity dependence is also reflected in the curve of the matrix condition numbers as shown in the FIG. 12. By making a least squares fitting of this curve, the condition number of the wavefront reconstruction matrix is obtained by $$cond_2(C^T C) = \begin{cases} -243.442 + 150.870 e^{\frac{t}{7.518}}, & t \text{ is odd} \\ -355.157 + 223.750 e^{\frac{t}{6.83}}, & t \text{ is even.} \end{cases} \tag{53}$$

When the matrix dimension becomes bigger, the Jacobi method converges slowly. It takes approximately 68000 iterations to obtain the eigenvalues with $10^{-7}$ accuracy for the case of t=15. At t=15 the maximum eigenvalue of 7.87 and the minimum eigenvalue of 0.009 are obtained, therefore the condition number is 865. Such a condition number indicates that the error propagation in wavefront estimation is stable and slow.

In support of the discussion above, the derivation of equations (11), (12), (26), and (27) above are presented. Denote $$\left.\frac{\partial^n W}{\partial y^n}\right|_i$$

as the n'th derivative of the wavefront at point i, and $$\left.\frac{\partial^n W}{\partial y^n}\right|_{i+\frac{1}{2}}$$

as the n'th derivative of the wavefront at the midpoint between the points i and i+1. According to Taylor's series $$w_i = w_{i+\frac{1}{2}} - \frac{a}{2}\frac{\partial W}{\partial y}\bigg|_{i+\frac{1}{2}} + \frac{a^2}{4\times 2!}\frac{\partial^2 W}{\partial y^2}\bigg|_{i+\frac{1}{2}} - \frac{a^3}{8\times 3!}\frac{\partial^3 W}{\partial y^3}\bigg|_{i+\frac{1}{2}} + \frac{a^4}{16\times 4!}\frac{\partial^4 W}{\partial y^4}\bigg|_{i+\frac{1}{2}} + O(a^5), \tag{A1}$$

and $$w_{i+1} = w_{i+\frac{1}{2}} + \frac{a}{2}\frac{\partial W}{\partial y}\bigg|_{i+\frac{1}{2}} + \frac{a^2}{4\times 2!}\frac{\partial^2 W}{\partial y^2}\bigg|_{i+\frac{1}{2}} + \tag{A2}$$

-continued $$\frac{a^3}{8 \times 3!} \frac{\partial^3 W}{\partial y^3}\bigg|_{i+\frac{1}{2}} + \frac{a^4}{16 \times 4!} \frac{\partial^4 W}{\partial y^4}\bigg|_{i+\frac{1}{2}} + O(a^5).$$

By subtracting Equation (A1) from (A2), $$w_{i+1} - w_i = a\frac{\partial W}{\partial y}\bigg|_{i+\frac{1}{2}} + \frac{a^3}{4 \times 3!} \frac{\partial^3 W}{\partial y^3}\bigg|_{i+\frac{1}{2}} + O(a^5). \tag{A3}$$

By adding Equation (A1) to (A2), $$w_{i+1} + w_i = 2w_{i+0.5} + \frac{a^2}{4} \frac{\partial^2 W}{\partial y^2}\bigg|_{i+\frac{1}{2}} + \frac{a^4}{8 \times 4!} \frac{\partial^4 W}{\partial y^4}\bigg|_{i+\frac{1}{2}} + O(a^6). \tag{A4}$$

The replacement of w with $$\frac{\partial W}{\partial y}$$

yields $$\frac{\partial W}{\partial y}\bigg|_{i+1} + \frac{\partial W}{\partial y}\bigg|_{i} = \tag{A5}$$

$$2\frac{\partial W}{\partial y}\bigg|_{i+\frac{1}{2}} + \frac{a^2}{4} \frac{\partial^3 W}{\partial y^3}\bigg|_{i+\frac{1}{2}} + \frac{a^4}{8 \times 4!} \frac{\partial^5 W}{\partial y^5}\bigg|_{i+\frac{1}{2}} + O(a^6).$$

Thus $$\frac{\partial W}{\partial y}\bigg|_{i+\frac{1}{2}} = \frac{1}{2}\left(\frac{\partial W}{\partial y}\bigg|_{i+1} + \frac{\partial W}{\partial y}\bigg|_{i}\right) - \frac{a^2}{8} \frac{\partial^3 W}{\partial y^3}\bigg|_{i+\frac{1}{2}} - \tag{A6}$$

$$\frac{a^4}{16 \times 4!} \frac{\partial^5 W}{\partial y^5}\bigg|_{i+\frac{1}{2}} + O(a^6).$$

And using Equation (A6), Equation (A3) may be expressed as $$w_{i+1} - w_i = \frac{a}{2}\left(\frac{\partial W}{\partial y}\bigg|_{i+1} + \frac{\partial W}{\partial y}\bigg|_{i}\right) - \frac{a^3}{12} \frac{\partial^3 W}{\partial y^3}\bigg|_{i+\frac{1}{2}} + O(a^5). \tag{A7}$$

Again, replace w with $$\frac{\partial W}{\partial y}$$

now in Equation (A7), to yield $$\frac{\partial W}{\partial y}\bigg|_{i+1} - \frac{\partial W}{\partial y}\bigg|_{i} = \frac{a}{2}\left(\frac{\partial^2 W}{\partial y^2}\bigg|_{i+1} + \frac{\partial^2 W}{\partial y^2}\bigg|_{i}\right) - \frac{a^3}{12} \frac{\partial^4 W}{\partial y^4}\bigg|_{i+\frac{1}{2}} + O(a^5). \tag{A8}$$

and $$w_{i+1} - 2w_i + w_{i-1} = a^2 \frac{\partial^2 W}{\partial y^2}\bigg|_{i} + \frac{a^4}{12} \frac{\partial^4 W}{\partial y^4}\bigg|_{i} + O(a^6), \tag{A9}$$

where $$\frac{\partial^2 W}{\partial y^2}\bigg|_{i} = \frac{w_{i+1} - 2w_i + w_{i-1}}{a^2} - \frac{a^2}{12} \frac{\partial^4 W}{\partial y^4}\bigg|_{i} + O(a^4). \tag{A10}$$

Combining Eq. (A10) and Eq. (A8)

$$\frac{\partial W}{\partial y}\bigg|_{i+1} - \frac{\partial W}{\partial y}\bigg|_{i} = \tag{A11}$$

$$\frac{a}{2}\left(\frac{w_{i+2} - 2w_{i+1} + w_i}{a^2} + \frac{w_{i+1} - 2w_i + w_{i-1}}{a^2}\right) -$$

$$\frac{a^3}{24}\left(\frac{\partial^4 W}{\partial y^4}\bigg|_{i} + \frac{\partial^4 W}{\partial y^4}\bigg|_{i+1}\right) - \frac{a^3}{12} \frac{\partial^4 W}{\partial y^4}\bigg|_{i+\frac{1}{2}} + O(a^5)$$

or $$\frac{\partial W}{\partial y}\bigg|_{i+1} - \frac{\partial W}{\partial y}\bigg|_{i} = \tag{A12}$$

$$\frac{1}{2a}(w_{i+2} - w_{i+1} - w_i + w_{i-1}) - \frac{a^3}{6} \frac{\partial^4 W}{\partial y^4}\bigg|_{i+\frac{1}{2}} + O(a^5).$$

Neglecting the higher order small-value terms on the right-hand side of Equation (A12), and denoting the first derivative of the wavefront in the y-direction as $s_y$, then $$s_{yi+2} - s_{yi+1} = \frac{1}{2a}(w_{i+3} - w_{i+2} - w_{i+1} + w_i), \tag{A13}$$

where i=1,2, . . . t−3; t+1,t+2, . . . 2t−3, . . . m−3.

Similarly in the z-direction, $$s_{z,i+t} - s_{z,i+2t} = \frac{1}{2a}(w_i - w_{i+t} - w_{i+2t} + w_{i+3t}), \tag{A14}$$

where i=1,2, . . . t, t+1,t+2, . . . 2t, . . . , m−3t.

A wavefront reconstruction algorithm suitable for practical use must have the following properties: (a) the wavefront estimates must be unbiased; (b) the error propagation coefficient must be slow; (c) the computation must be efficient, especially for large datasets, and the necessary memory space should be small enough to be applicable in the laboratory; finally, (d) the algorithm should be easily adaptable to various pupil shapes. In the present invention, a Gerchberg-Saxton type iterative process was combined with a linear least-squares method to obtain a practical unbiased wavefront estimation algorithm that combines the accuracy of the iterative wavefront extrapolation technique with the linear sparse matrix efficiency. With the domain extension technique, a universal wavefront reconstruction matrix and the associated universal slope-computation matrices were obtained for any pupil shape, and the matrix coefficients are fully determined and known once and for all. An analysis of error propagation shows that the wavefront reconstruction matrix is well-conditioned, yielding low propagation errors.

This invention has applications in such diverse fields as ophthalmometry, optical astronomy, laser beam profiling, optical component testing, and microscopy.

This invention is particularly applicable in the field of adaptive optics in which the components of an optical system are actively manipulated to maintain high image quality. By example, the resolution of ground-based telescopes is highly dependent on the amount of atmospheric turbulence present, as this causes distortion of the wavefront and thus a reduction in image quality. In an adaptive optical system atmospheric distortion is measured by a wavefront sensor which then provides a control signal based on the reconstructed wavefront for corrective optics such as deformable mirrors. Such a system typically has to work at speeds sufficient to keep up with the rapid atmospheric changes.

In ophthalmometry, wavefront sensing and reconstruction is increasingly being used to characterize higher-order aberrations in the human eye, providing vital information for corrective eye surgery.

Wavefront sensing and reconstruction also has application in testing individual optical components, such as mirrors and lenses. The information obtained from a reconstructed wavefront can lead to reduced development times, reduced component cost, and improved optical performance.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A method for wavefront reconstruction comprising the steps of:
   (a) obtaining slope-type data from a wavefront sensor;
   (b) embedding an irregular pupil to a regular square domain and setting the slopes outside the pupil to zero;
   (c) computing a wavefront estimation for the square domain;
   (d) computing slopes of the computed wavefront;
   (e) replacing the slopes in original pupil region with original raw slope data; and
   (f) iteratively computing for the whole extended square domain until the wavefront difference between two consecutive iterations is less than a set threshold value.

2. The method of claim 1 wherein said wavefront sensor is selected from at least one of a slope sensor such as a Shack-Hartmann sensor, shear interferometer, and a slope-type sensor.

3. The method of claim 1 wherein said slope data is selected from one of: gradients data, wavefront differences data, and slope-type data.

4. The method of claim 1 wherein said regular square domain refers to a square grid array that is indexed from one of sequentially, and column by column.

5. The method of claim 1 wherein said regular square domain is bigger than the original pupil so that it can embrace the original pupil.

6. The method of claim 1 wherein said the wavefront computation and slope extraction computations use wavefront reconstruction geometry.

7. The method of claim 6, wherein the wavefront reconstruction geometry is selected from one of: Southwell, Hudgin, and Fried models.

8. The method of claim 1 wherein the step of computing the wavefront from slope data and slope data from the computed wavefront includes using Gerchberg-type iterations.

9. The method of claim 1 wherein the step of computing the wavefront from slope data and slope data from wavefront and replacing the original slope data back into the original pupil includes using wavefront extrapolations.

10. The method of claim 1 wherein the step of computing the wavefront and slopes includes: linear sparse normal matrix equations.

11. The method of claim 1 wherein the matrices for computing the wavefront and slopesincludes one of: full-rank matrices, and rank-deficient matrices depending on reconstruction geometry.

12. The method of claim 11, wherein the reconstruction geometry is selected from one of: Hudgin, Southwell, and Fried geometries.

13. The method of claim 1 wherein said the wavefront difference includes:
   wavefront slope.

14. An iterative system for wavefront reconstruction comprising:
   means for obaining slope-type data from a wavefront sensor;
   means for embedding an irregular pupil to a regular square domain and setting the slopes outside the pupil to zero;
   means for determining a wavefront estimation for the square domain;
   means for determining slopes of the wavefront estimation;
   means for replacing the slopes in original pupil region with original raw slope data; and
   means for iteratively determining for the whole extended square domain until the wavefront difference between two consecutive iterations is less than a set threshold value.

* * * * *